US010603503B2

United States Patent
Pakhomov et al.

(10) Patent No.: US 10,603,503 B2
(45) Date of Patent: Mar. 31, 2020

(54) LOW-ENERGY DEFIBRILLATION WITH NANOSECOND PULSED ELECTRIC FIELDS

(71) Applicant: Old Dominion University Research Foundation, Norfolk, VA (US)

(72) Inventors: Andrei G. Pakhomov, Norfolk, VA (US); Christian W. Zemlin, Norfolk, VA (US)

(73) Assignee: OLD DOMINION UNIVERSITY RESEARCH FOUNDATION, Norfolk, VA (US)

(*) Notice: Subject to any disclaimer, the term of this patent is extended or adjusted under 35 U.S.C. 154(b) by 13 days.

(21) Appl. No.: 15/554,808

(22) PCT Filed: Mar. 2, 2016

(86) PCT No.: PCT/US2016/020504
§ 371 (c)(1),
(2) Date: Aug. 31, 2017

(87) PCT Pub. No.: WO2016/141096
PCT Pub. Date: Sep. 9, 2016

(65) Prior Publication Data
US 2018/0050215 A1 Feb. 22, 2018

Related U.S. Application Data

(60) Provisional application No. 62/127,462, filed on Mar. 3, 2015.

(51) Int. Cl.
*A61N 1/39* (2006.01)
*A61N 1/32* (2006.01)

(52) U.S. Cl.
CPC ............ *A61N 1/3906* (2013.01); *A61N 1/327* (2013.01)

(58) Field of Classification Search
CPC ......... A61N 1/39; A61N 1/3906; A61N 1/327
See application file for complete search history.

(56) References Cited

U.S. PATENT DOCUMENTS

| 4,946,793 | A | * | 8/1990 | Marshall, III | ......... | B01D 57/02 |
| | | | | | | 435/173.6 |
| 5,720,767 | A | * | 2/1998 | Amely-Velez | ....... | A61N 1/3931 |
| | | | | | | 607/5 |

(Continued)

FOREIGN PATENT DOCUMENTS

WO    2006/052838 A2    5/2006
WO    2011/159641 A1    12/2011

(Continued)

OTHER PUBLICATIONS

International Search Report and Written Opinion dated May 11, 2016 in corresponding PCT application PCT/US2016/020504, 9 pages.

(Continued)

*Primary Examiner* — Catherine M Voorhees
(74) *Attorney, Agent, or Firm* — MH2 Technology Law Group, LLP

(57) ABSTRACT

Methods for terminating fibrillation in a fibrillating heart employing nanosecond pulsed electric fields (nsPEFs) are disclosed. nsPEF defibrillation demonstrates its effectiveness as a new defibrillation modality, achieving reliable defibrillation with energies that are an order of magnitude lower than those needed for conventional defibrillation (millisecond shocks with mono- and bi-phasic waveforms). Tests did not reveal any negative effect of nsPEF defibrillation on cardiac tissue, in particular, cardiac tissue treated with nsPEFs does not exhibit a baseline shift in the optical transmembrane potential signal (distinctive feature that indicates electroporation), or changes in action potential duration or shape. The mechanism of nsPEF defibrillation is (Continued)

likely different from conventional defibrillation since it does not rely on membrane charging but on the basis of displacement currents that flow within nanoseconds after the shock is applied. nsPEFs provide the technology for the next generation of defibrillators that help emergency medical services to treat patients effectively.

19 Claims, 13 Drawing Sheets

(56) References Cited

U.S. PATENT DOCUMENTS

| | | | |
|---|---|---|---|
| 5,733,889 A | 3/1998 | Brown | |
| 7,470,240 B2 | 12/2008 | Schultheiss et al. | |
| 2010/0023004 A1* | 1/2010 | Francischelli | A61B 18/1442 606/41 |
| 2011/0152956 A1 | 6/2011 | Hincapie Ordonez et al. | |
| 2012/0032522 A1* | 2/2012 | Schatz | H02J 50/70 307/104 |
| 2012/0191150 A1* | 7/2012 | Kameli | A61N 1/375 607/4 |
| 2012/0310315 A1* | 12/2012 | Savage | A61N 1/39 607/116 |
| 2013/0260435 A1* | 10/2013 | Pakhomova | C12N 13/00 435/173.6 |
| 2015/0088212 A1* | 3/2015 | De Ridder | A61N 1/0529 607/2 |
| 2015/0201991 A1* | 7/2015 | Zemlin | A61B 18/1492 606/41 |
| 2017/0326361 A1* | 11/2017 | Kreis | A61B 18/14 |

FOREIGN PATENT DOCUMENTS

| | | | |
|---|---|---|---|
| WO | WO-2011159641 A1 * | 12/2011 | A61N 1/3627 |
| WO | 2012/071526 A2 | 5/2012 | |

OTHER PUBLICATIONS

Go et al., Heart Disease and Stroke Statistics—2014 Update: A Report From the American Heart Association, Circulation 129(3), 2014, pp. e28-e292.
Nichol et al., Regional Variation in Out-of-Hospital Cardiac Arrest Incidence and Outcome, JAMA: the journal of the American Medical Association 300(12), Sep. 24, 2008, pp. 1423-1431.
Sowell et al., Ionic Mechanism of Shock-Induced Arrhythmias: Role of Intracellular Calcium, Heart Rhythm 9(1), Jan. 2012, pp. 96-104.
Goncalves et al., Inappropriate Shocks in Patients with ICDs: Single Chamber versus Dual Chamber, Arq Bras Cardiol 101(2), 2013, pp. 141-148.
Al-Khadra et al., The Role of Electroporation in Defibrillation, Circ Res 87(9), 2000, pp. 797-804.
Nikolski et al., Electroporation of the heart, Europace 7, 2005, pp. S146-S154.
Wang et al., Electroporation induced by internal defibrillation shock with and without recovery in intact rabbit hearts, Am J Physiol Heart Circ Physiol 303, 2012, pp. H439-H449.
Tan et al., Impact of Programming Strategies Aimed at Reducing Nonessential Implantable Cardioverter Defibrillator Therapies on Mortality A Systematic Review and Meta-Analysis, Circulation: Arrhythmia and Electrophysiology 7, 2014, pp. 164-170.
Tokano et al., Effect of Ventricular Shock Strength on Cardiac Hemodynamics, Journal of Cardiovascular Electrophyslology vol. 9, No. 8, Aug. 1998, pp. 791-797.
Xie et al., High-Energy Defibrillation Increases the Severity of Postresuscitation Myocardial Dysfunction, Circulation 96, 1997, pp. 683-688.
Rosenheck et al., Modified alternating current defibrillation: a new defibrillation technique, Europace 11, 2009, pp. 239-244.
Bradfield et al., Interventions to decrease the morbidity and mortality associated with implantable carioverter-defibrillator shocks, Curr Opin Crit Care, 18(5), 2012, pp. 432-437.
Clark et al., Transthoracic biphasic waveform defibrillation at very high and very low energies: a comparison with monophasic waveforms in an animal model of ventricular fibrillation, Resuscitation 54, 2002, pp. 183-186.
Didon et al., Clinical experience with a low-energy pulsed biphasic waveform in out-of-hospital cardiac arrest, Resuscitation 76, 2008, pp. 350-353.
Gray et al., Cardiovascular Disease, Several small shocks beat one big one, Nature 475(7355), 2011, pp. 181-182.
Kodama et al., Arrhythmogenic changes in action potential configuration in the ventricle induced by DC shocks, Journal of Electrocardiology, vol. 32, 1999, pp. 92-99.
Sandeep V. Pandit, Phd, Alternating current for defibrillation therapy:Time for reconsideration?, Heart Rhythm 10 (5), 2013, pp. 749-750.
Tibbals et al., External and internal biphasic direct current shock doses for pediatric ventricular fibrillation and pulseless ventricular tachycardia, Pediatr Crit Care Med 2011 vol. 12, No. 1, pp. 14-20.
Weinberg et al., Defibrillation success with high frequency electric fields is related to degree and location of conduction block, Heart Rhythm 10(5), 2013, pp. 740-748.
Kodama et al., Regional Differences in Arrhythmogenic Aftereffects of High Intensity DC Stimulation in the Ventricles, Pace 23(5), 2000, pp. 807-817.
KB Kern, Postresuscitation Myocardial Dysfunction, Cardiology Clinics, 20(1), 2002, pp. 89-101.
Tewelde et al., Cooling the Fire Resuscitated Sudden Death, Cardiol Clin 30 (2012), pp. 639-650.
Roberts et al., The Defibrillation Efficacy of High Frequency Alternating Current Sinusoidal Waveforms in Guinea Pigs, PACE,vol. 26, Part 1, Feb. 2003, pp. 599-604.
Berg et al., Attenuating the defibrillation dosage decreases postresuscitation myocardial dysfunction in a swine model of pediatric ventricular fibrillation, Pediatr Crit Care Med. 9(4), Jul. 2008, pp. 429-434.
Laurent et al., Reversible Myocardial Dysfunction in Survivors of Out-of-Hospital Cardiac Arrest, Journal of the American College of Cardiology, vol. 40, No. 12, 2002, pp. 2110-2116.
Rantner et al., Terminating Ventricular Tachyarrhythmias Using Far-Field Low-Voltage Stimuli: Mechanisms and Delivery Protocols, Heart Rhythm 10(8), Aug. 2013, pp. 1209-1217.
Luther et al., Low-energy control of electrical turbulence in the heart, Nature, vol. 475, Jul. 14, 2011, pp. 235-239.
Van Rees et al., Inappropriate Implantable Cardioverter-Defibrillator Shocks Incidence, Predictors, and Impact on Mortality, Journal of the American College of Cardiology, vol. 57, No. 5, 2011, pp. 556-562.
Tzeis et al., Tools and strategies for the reduction of inappropriate implantable cardioverter defibrillator shocks, Europace 10, 2008, pp. 1256-1265.
Tang et al., A Comparison of Biphasic and Monophasic Waveform Defibrillation After Prolonged Ventricular Fibrillation, Chest 120(3), Sep. 2001, pp. 948-954.
Kudenchuk et al., Transthoracic Incremental Monophasic Versus Biphasic Defibrillation by Emergency Responders (TIMBER): A Randomized Comparison of Monophasic With Biphasic Waveform Ascending Energy Defibrillation for the Resuscitation of Out-of-Hospital Cardiac Arrest due to Ventricular Fibrillation, Circulation 114(19), 2006, pp. 2010-2018.
Mittal et al., Comparison of a Novel Rectilinear Biphasic Waveform With a Damped Sine Wave Monophasic Waveform for Transthoracic Ventricular Defibrillation, Journal of the American College of Cardiology, vol. 34, No. 5, 1999, pp. 1595-1601.
Tanabe et al., Comparison of Outcomes After Use of Biphasic or Monophasic Defibrillators Among Out-of-Hospital Cardiac Arrest Patients a Nationwide Population-Based Observational Study, Circ Cardiovasc Qual Outcomes 5(5), Sep. 2012, pp. 689-696.

* cited by examiner

LOW-ENERGY DEFIBRILLATION WITH NANOSECOND PULSED ELECTRIC FIELDS

CROSS-REFERENCE TO RELATED APPLICATIONS

This application is a U.S. National Stage application of PCT/US2016/020504 filed Mar. 2, 2016, which claims priority to U.S. Provisional Application Ser. No. 62/127,462 filed Mar. 3, 2015, the entire disclosures of which are hereby incorporated by reference in their entireties.

BACKGROUND

Field of the Disclosure

The present disclosure relates generally to defibrillation, and more specifically, to systems and methods for heart defibrillation using nanosecond pulsed electric fields.

Background Information

The American Heart Association (AHA) estimates that each year about 420,000 people in the United States experience Emergency Medical Service (EMS)-assessed out-of-hospital cardiac arrests [1]. Among them 23% have an initial rhythm of ventricular fibrillation (VF) or ventricular tachycardia (VT) or are shockable by an automated external defibrillator [1-2]. For decades, the most common lifesaving procedure for terminating VF and VT is by applying an intense electric shock, conventionally known as defibrillation.

Defibrillation is applied employing an electric circuit known as defibrillator. When defibrillators first became widely available during the 60's, they used a heavily damped sinusoidal waveform that was essentially monophasic, and research was focused on reducing the peak voltage, current, and total energy to minimize collateral damage to the cardiac tissue since electrical shocks above a critical amplitude can damage cells. Adverse effects of defibrillation, especially at higher energy levels, may include cell damage, pain and anxiety, cardiac ectopy, tachycardia, arrhythmia, asystole, re-fibrillation, and increased mortality [3-13]. Furthermore, increasing the defibrillation dose worsens post-resuscitation myocardial dysfunction [14-16], one of the key components of the high-mortality post-cardiac arrest syndrome [17-19].

Over the past few decades, a significant effort has been made on improving the efficacy and reducing the delivered energy for defibrillation. During the 1990's, the monophasic shocks were replaced by biphasic shocks. Biphasic shocks are now generally regarded as superior and universally employed in modern defibrillators. Typical reductions in the energy made possible by the use of biphasic waveforms are in the order of 20-40%. Several studies have tested improved biphasic waveforms methodologies that further reduce the required defibrillation energy, but these results have indicated only marginal improvements.

Recent studies on reducing defibrillation energy have been directed to using multiple shocks of reduced amplitude while keeping pulse durations in the low millisecond range. The aforementioned studies illustrate that these defibrillation treatments reduce defibrillation energies 50-80% below typical biphasic shocks [20-22].

Additionally, the first shock from the automated external defibrillator does not always terminate VF or restore the organized rhythm. Up to 50% of patients required 1-8 additional shocks [23] or 2.7±2.4 shocks per patient [24]. Between 10 and approximately 30% of patients with an implantable cardioverter defibrillator (ICD) receive one or more inappropriate shocks [25-26]. There is a tradeoff between keeping the shock amplitude low (risking the need for multiple attempts) and keeping the number of shocks low by starting with a high-amplitude shock (foregoing the chance to defibrillate with lower amplitude). In clinical practice, patients often receive several shocks which delay the defibrillation and decrease the chances for survival even if cardiopulmonary resuscitation is performed.

Although modern defibrillation techniques are reasonably efficient and safe, there is a widely recognized need for defibrillation methods with lower energy deposition that is generally associated with lower tissue damage. The quest for more efficient yet safer defibrillation resulted in the transition from monophasic to biphasic waveforms [27-31]. It also motivates ongoing research into low-energy defibrillation strategies [3, 32, 33] and the controlled cardiac conduction block using high-frequency electrostimulation [34-37].

Accordingly, there is a need for more efficient, safe, and reliable methods for defibrillation that employ reduced energy as well as decreased number of shocks delivered to patients.

SUMMARY

One or more aspects of the present disclosure provide methods for terminating fibrillation in a fibrillating heart employing nanosecond pulsed electric fields (nsPEFs).

In some embodiments, when employing nsPEFs, the defibrillation energy is reduced by increasing the shock amplitude but dramatically decreasing its duration. In these embodiments, nsPEF defibrillation can reduce the required defibrillation energy by up to 10 times when compared to conventional methods. Further to these embodiments, the electrical energy deposited into the heart after delivery of the therapeutic dose is in the range of about 1 mJ to about 500 J. In these embodiments, the electric pulses employed to generate nsPEFs may use a pulse duration from about 1 ns to about 1000 ns with pulse amplitudes ranging from about 0.01 kV to about 100 kV.

In some embodiments, nsPEFs induce transmembrane voltage using a different mechanism than conventional millisecond shocks. In these embodiments, the nsPEFs shock-induced transmembrane voltage is a result of displacement currents making a greater contribution to the membrane potential.

In some embodiments, nsPEFs interact with living matter using dielectric displacement, thereby allowing deeper penetration of the electric fields (e-fields) and more uniform activation of tissue. In these embodiments, deeper penetration of the e-fields and more uniform activation of tissue are critical advantages for defibrillation. Further to these embodiments, as a result of the aforementioned critical advantages, nsPEF defibrillation is less susceptible to inhomogeneities and provides uniform and simultaneous activation of cardiomyocytes.

In some embodiments, nsPEF defibrillation causes cell membrane nanoelectroporation whereas conventional methods employ long-pulses that cause electroporation. In these embodiments, pores within the cell membrane opened by nsPEFs are smaller in diameter than those opened by long pulses. Further to these embodiments, the pores opened by nsPEFs within cell membranes grow in diameter while the externally applied voltage is still on, and the briefness of nsPEFs does not allow pore expansion. In these embodiments, the smaller pore size resulting from nsPEFs greatly limits the transmembrane traffic through the pores and reduces the loss of critical solutes by the cell, thereby making nanoelectroporation less injurious than long-pulse electroporation.

In some embodiments, nsPEFs relies on displacement currents rather than on the conduction currents to reach the excitation transmembrane potential (TMP), thereby significant energy savings are achieved. In these embodiments, energy savings are even higher within syncytial tissue where large amounts of energy can be expended on the conductive currents between cells, thus the energy needed for nsPEF defibrillation is dramatically reduced.

In some embodiments, nsPEF defibrillation elicits action potentials (APs) in nerve and muscle cells substantially similar to conventional longer electric pulses. In these embodiments, voltage thresholds become higher as the pulses are made shorter; however, high-rate nsPEF pulse trains can elicit APs at low amplitudes, even at very short pulse durations. Further to these embodiments, nsPEFs at amplitudes below the AP thresholds do not cause harmful biological effects, thereby enabling nsPEFs for safer defibrillation applications. Still further to these embodiments, because the electric fields for nsPEF stimulation may reach hundreds V/cm and even tens of kV/cm at the nanosecond duration, such pulses may still be at or under the threshold for any harmful bioeffects or unpleasant sensations. In these embodiments, even at electroporating nsPEF intensities, considerable thermal effects (>1° C.) are not produced. Further to these embodiments, the non-ionizing energy delivered by nsPEFs is insufficient to break any chemical bonds even at hundreds kV/cm.

In some embodiments, successful defibrillation is achieved when applying nsPEF shocks in which the energy dissipated into the tissue is less than 64 mJ. In an example, the energy dissipated into the tissue (56 mJ±4 mJ) is calculated based on the formula ($½CU^2$), wherein U is the amplitude of a nsPEF shock (e.g., U=2.3 kV±0.2 kV) and C is the capacitance of the capacitor energy source (e.g., C=21.2 nF). In summary, the energy deposited at the defibrillation threshold was 56 mJ±4 mJ, or approximately 11% of the energy needed for defibrillation with a biphasic ms pulse.

In some embodiments, a variety of markers and/or measurements are used for evaluating tissue, before and after the shock, to determine heart functionality and/or tissue damage from nsPEF treatment.

In some embodiments, action potential duration (APD) and diastolic interval (DI) are measured before and after a nsPEF shock application to determine if any changes occurred in the electrical activity of the heart. In these embodiments, the absence of significant permanent changes in APD and DI indicate that the normal physiological electrical activity of the heart is not affected by nsPEF shocks.

In some embodiments, a method of treating cardiac arrhythmias is provided. The method may comprise delivering electrical stimulation to a heart experiencing an arrhythmia, the electrical stimulation comprising at least one or more electrical pulses having a pulse duration from about 1 nanoseconds to about 1,000 nanoseconds, and further having pulse amplitudes ranging from about 0.01 kV to about 100 kV, in a manner sufficient to restore normal electrical activity of the heart. According to one aspect of the method, displacement currents flowing after electrical stimulation may result in changes in transmembrane voltage of the heart. According to another aspect of the method, electrical energy deposited into the heart after electrical stimulation may be in the range of about 1 mJ to about 500 J. According to still another aspect of the method, the electrical stimulation may reversibly open pores within cell membranes. These pores may be cation-selective, and may result in membrane hyperpolarization and reduced excitability. In still another aspect, the electrical stimulation may reduce whole-cell currents through voltage gated Na+ and Ca2+ channels.

Further still, according to one aspect of the method, no permanent changes in action potential duration may occur after restoring normal electrical activity of the heart by the electrical stimulation. According to another aspect, no permanent changes in diastolic interval may occur after restoring normal electrical activity of the heart by the electrical stimulation. According to still another aspect, no tissue damage or tissue death may occur after restoring normal electrical activity of the heart by the electrical stimulation. In some embodiments, the arrhythmia may comprise ventricular fibrillation or ventricular tachycardia.

In some embodiments, a method for treating cardiac arrhythmias is provided. The method may comprise delivering a therapeutic dose of electric current to a heart experiencing an arrhythmia sufficient to restore normal electrical activity of the heart, wherein the therapeutic dose comprises applying one or more nanosecond pulsed electric fields having a pulse duration from about 1 nanoseconds to about 1,000 nanoseconds, and further having pulse amplitudes ranging from about 0.01 kV to about 100 kV. According to one aspect of the method, displacement currents flowing after delivery of the therapeutic dose may result in changes in transmembrane voltage of the heart. According to another aspect of the method, electrical energy deposited into the heart after delivery of the therapeutic dose may be in the range of about 1 mJ to about 500 J. According to still another aspect of the method, delivery of the therapeutic dose may reversibly open pores within cell membranes. These pores may be cation-selective, and may result in membrane hyperpolarization and reduced excitability. In still another aspect, delivery of the therapeutic dose may reduce whole-cell currents through voltage gated Na+ and Ca2+ channels.

Further still, according to one aspect of the method, no permanent changes in action potential duration may occur after restoring normal electrical activity of the heart by the therapeutic dose. According to another aspect, no permanent changes in diastolic interval may occur after restoring normal electrical activity of the heart by the therapeutic dose. According to still another aspect, no tissue damage or tissue death may occur after restoring normal electrical activity of the heart by the therapeutic dose.

In summary, nsPEF defibrillation demonstrates its effectiveness as a new defibrillation modality, thereby achieving reliable defibrillation with energies that are an order of magnitude smaller than those needed for conventional defibrillation (e.g., mono and bi-phasic waveforms). Further, nsPEF defibrillation did not negatively affect tissue, did not exhibit a baseline shift within the optical transmembrane potential signal (a distinctive feature which indicates electroporation), or affect the APD or shape. Additionally, the DI following a shock-induced activation was notably prolonged, but only for a single beat. Finally, the mechanism for nsPEF defibrillation is different from conventional defibrillation since it does not rely on membrane charging, but on the basis of displacement currents that flow within nanoseconds after the shock is applied.

DETAILED DESCRIPTION

Figure 1A:
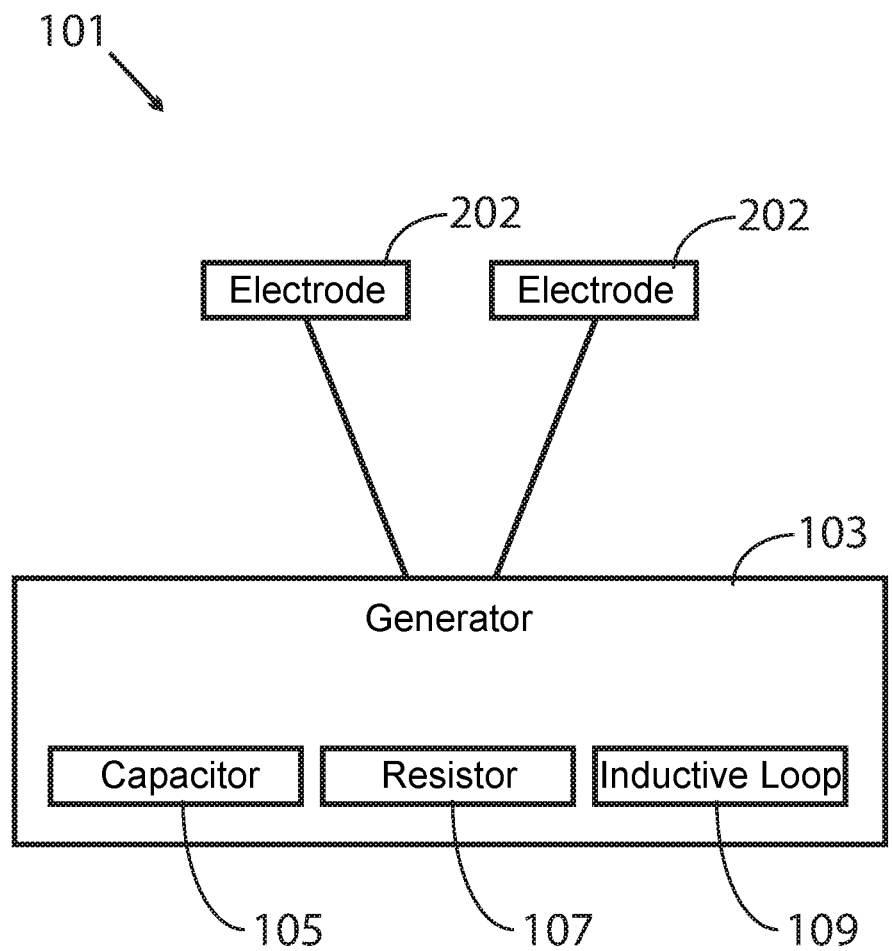
FIG. 1A is a schematic diagram of an exemplary system suitable for use with certain embodiments disclosed herein.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the disclosure. One having ordinary skill in the relevant art, however, will readily recognize that the embodiments of the disclosure can be practiced without one or more of the specific details or with other methods. In other instances, well-known structures or operations are not shown in detail to avoid obscuring the aspects of the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

Definitions

As used here, the following terms have the following definitions:

"Arrhythmia" refers to a problem with the rate or the rhythm of the heartbeat.

"Electroporation or electroporated" refers to a physical method that uses an electrical pulse to create pores in cell membranes.

"Langendorff system" refers to a predominant in vitro technique used in pharmacological and physiological research employing isolated animal hearts, thereby allowing the examination of cardiac contractile strength and heart rate without the complications of an intact animal.

"Nanoelectroporation" refers to a physical method that uses an electrical pulse of nanosecond duration to create transient nanopores in cell membranes.

"Nanosecond pulsed electric fields (nsPEFs)" refers to electric pulses of nanosecond duration.

DESCRIPTION OF THE DISCLOSURE

For the purposes of promoting an understanding of the principles of the disclosure, reference will now be made to preferred embodiments and specific language will be used to describe the same. It will nevertheless be understood that no limitation of the scope of the disclosure is thereby intended. Rather, such alterations and further modifications of the disclosure, and such further applications of the principles of the disclosure as illustrated herein, as would be contemplated by one having skill in the art to which the disclosure relates are intended to be part of the present disclosure.

In view of the limitations of existing defibrillation methods, the various embodiments in the present disclosure are directed to new methods to terminate fibrillation in a fibrillating heart employing nanosecond pulsed electric fields (nsPEFs).

In some embodiments, when employing nsPEFs, the defibrillation energy is reduced by increasing the shock amplitude but dramatically decreasing its duration. In these embodiments, nsPEF defibrillation can reduce the required defibrillation energy by up to 10 times when compared to conventional methods. Further to these embodiments, the electrical energy deposited into the heart after delivery of the therapeutic dose is in the range of about 1 mJ to about 500 J. In these embodiments, the electric pulses employed to generate nsPEFs may use a pulse duration from about 1 ns to about 1000 ns with pulse amplitudes ranging from about 0.01 kV to about 100 kV.

Mechanism of nsPEF Defibrillation

In conventional millisecond shocks, most of the shock-induced transmembrane voltage is the result of cell membrane charging and then discharging. Further, when an electric field is applied to cardiac tissue, two different mechanisms affect the transmembrane potentials of the myocytes in the tissue; first the immediate applied field, and then the charging of the membrane, which is the main effect for conventional defibrillation.

In some embodiments, nsPEFs induce transmembrane voltage using a different mechanism than conventional millisecond shocks. In these embodiments, the nsPEFs shock-induced transmembrane voltage is a result of displacement currents making a greater contribution to the membrane potential. Further to these embodiments, theoretical estimates suggest that the dominant effect for nsPEFs is membrane potential induction via a displacement current while for conventional defibrillation, membrane charging is dominating.

In some embodiments, nsPEFs interact with living matter using dielectric displacement, thereby allowing deeper penetration of the electric fields (e-fields) and more uniform activation of tissue. In these embodiments, deeper penetration of the e-fields and more uniform activation of tissue are critical advantages for defibrillation. Further to these embodiments, as a result of the aforementioned critical advantages, nsPEF defibrillation is less susceptible to inhomogeneities and provides uniform and simultaneous activation of cardiomyocytes.

In some embodiments, nsPEFs provide more efficient defibrillation when compared to conventional methods. In these embodiments, nsPEF stimuli are too brief for capacitive charging and displacement currents dominate over conduction currents, thereby intercellular electric connections do not affect membrane charging and every cell, even in the syncytial tissue, behaves as an independent entity. Further to these embodiments, this behavior is electrically equivalent to each cell having its own virtual cathode, and excitation is not affected by the vicinity to the cathode, instead, all cells within a high enough electric field area are excited simultaneously thereby eliminating the chance of re-initiating fibrillation.

In some embodiments, nsPEF defibrillation causes cell membrane nanoelectroporation whereas conventional methods employ long-pulses that cause electroporation. In these embodiments, pores within the cell membrane opened by nsPEFs are smaller in diameter than those opened by long pulses. Further to these embodiments, the pores opened by nsPEFs within cell membranes grow in diameter while the externally applied voltage is still on, and the briefness of nsPEFs does not allow for pore expansion. Still further to these embodiments, the diameter of nsPEF-opened pores, as estimated by different conventional methods, does not exceed 1-1.5 nanometers ("nanoelectroporation"), whereas pores opened by millisecond-duration pulses can reach several or tens of nanometers. In these embodiments, the smaller pore size resulting from nsPEFs greatly limits the transmembrane traffic through the pores and reduces the loss of critical solutes by the cell, thereby making nanoelectroporation less injurious than long-pulse electroporation. Further to these embodiments, nanoelectropores exhibit unique conductive properties and are cation-selective, thereby having the highest permeability to $K^+$. In these embodiments, creating nanopores is substantially similar to the opening of $K^+$ ion channels, which can lead to membrane hyperpolarization and reduction of excitability. Further to these embodiments, nsPEFs reduce whole-cell currents through voltage gated $Na^+$ and $Ca^{2+}$ channels, which may contribute to nsPEF anti-arrhythmic effect.

In some embodiments, since nsPEFs do not rely on the conduction currents to reach the excitation transmembrane potential (TMP), significant energy savings are achieved. In these embodiments, energy savings are even higher within syncytial tissue where large amounts of energy can be expended on the conductive currents between cells, thus the energy needed for nsPEF defibrillation is dramatically reduced.

In some embodiments, nsPEF defibrillation elicits action potentials (APs) in nerve and muscle cells substantially similar to conventional longer electric pulses. In these embodiments, voltage thresholds become higher as the pulses are made shorter; however, high-rate nsPEF pulse trains can elicit APs at low amplitudes, even at very short pulse durations. Further to these embodiments, nsPEFs at amplitudes below the AP thresholds do not cause harmful biological effects, thereby enabling nsPEFs for safer defibrillation applications. Still further to these embodiments, because the electric fields for nsPEF stimulation may reach hundreds V/cm and even tens of kV/cm at the nanosecond duration, such pulses may still be at or under the threshold for any harmful bioeffects or unpleasant sensations. In these embodiments, even at electroporating nsPEF intensities, considerable thermal effects (>1° C.) are not produced. Further to these embodiments, nsPEF is a non-ionizing radiation and its delivered energy is insufficient to break any chemical bonds even at hundreds kV/cm.

Reference will now be made to specific examples illustrating the use of nsPEFs for defibrillation. It is to be understood that the examples are provided to illustrate preferred embodiments and that no limitation of the scope of the disclosure is intended thereby.

EXAMPLES

Materials and Methods

Langendorff-perfused rabbit hearts were employed for the following examples. All animals were treated according to the U.S. Guide for the Care and Use of Laboratory Animals, and all procedures where approved by the U.S. Institutional Animal Care and Use Committee.

In some embodiments as in the exemplary system 101 shown in FIG. 1A, the nsPEF generator 103 employed is designed as a transmission line generator employing a 30 m length of a double shielded coaxial cable (RG-217U) as a capacitor (C=21.2 nF) 105. In these embodiments, an additional resistor Zm=13.7Ω 107 was placed in parallel with the heart to achieve impedance matching between the transmission line and the load. Further to these embodiments, this setup charges the transmission line until the breakdown voltage of the spark gap is reached and then rectangular pulses are applied having a duration of t=2 l/v to the load, where l is the length of the transmission line and v the speed of light in the transmission line. Still further to these embodiments, l=30 m, v=0.66 c (where c is the speed of light), and consequently, t≈300 ns. In these embodiments, defibrillation shocks are detected with an inductive loop placed close to the spark gap; the inductive loop 109 is connected to an analog/digital converter whose output is written into a corner pixel of the optical mapping movies as they are recorded.

Optical Mapping System

Figure 1B:
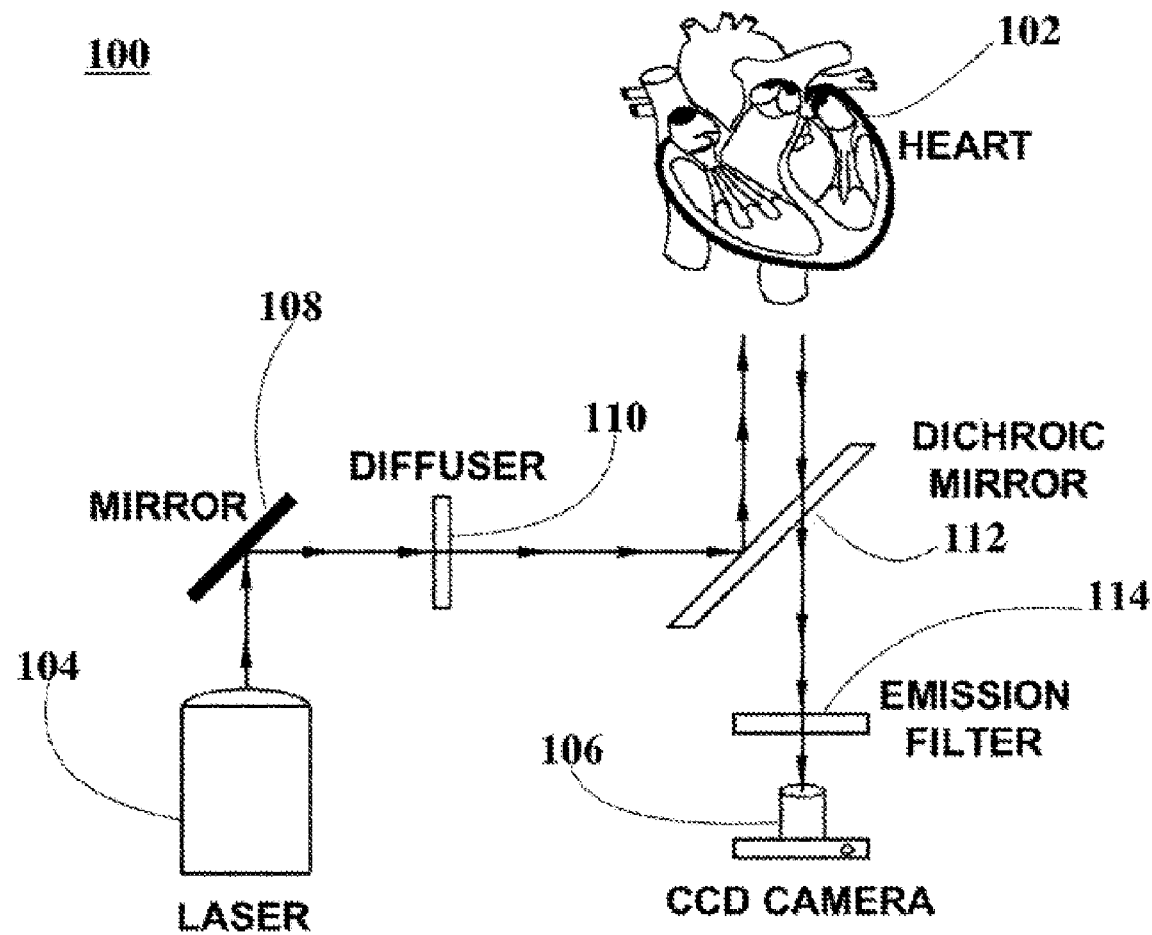
FIG. 1B is a graphical representation illustrating a system for optical mapping of a heart, according to an embodiment.

FIG. 1B is a graphical representation illustrating a system for optical mapping of a heart, according to an embodiment. In FIG. 1B, optical mapping system 100 includes Langendorff-perfused heart 102, laser source 104, CCD camera 106, mirror 108, diffuser 110, dichroic mirror 112, and emission filter 114.

Example 1

Three (3) New Zealand white rabbits were handled and euthanized according to the approved animal protocol. The three rabbits were heparinized (500 IU/kg) and brought to a surgical plane of anesthesia with 2.5-4% isoflurane. The hearts were surgically removed, the aorta immediately cannulated, and the hearts flushed with and immersed in cold cardioplegic solution (in mM: glucose 280, KCl 13.4, $NaHCO_3$ 12.6, mannitol 34). The hearts were placed within optical mapping system 100 and retrogradely perfused with Tyrode solution (in mM: NaCl: 130, KCl: 4.0, $CaCl_2$: 1.8, $MgCl_2$: 1.0, $NaHCO_3$: 24, $NaH_2PO_4$: 1.2, glucose: 5.6) bubbled with 95% $O_2$/5% $CO_2$, at a pressure of 60-80 mmHg, with pH kept between 7.35 and 7.45 and temperature of about 37.5±0.5° C.

In an example, Langendorff-perfused heart 102 is injected with 5 mL bolus of the voltage-sensitive fluorescent probe Di-4-ANBDQBS (about 10 μM). In this example, an electromechanical uncoupler blebbistatin inhibitor (about 10 μmol/L) is added to the Tyrode solution to reduce motion artifacts. In some embodiments, Langendorff-perfused heart 102 is illuminated with a laser light from laser source 104 directed to mirror 108 and then through diffuser 110 and then reflected by a dichroic mirror 112 onto Langendorff-perfused heart 102 to achieve uniform illumination. In these embodiments, upon reaching Langendorff-perfused heart 102 and illuminating it, a portion of the laser light is absorbed and caused the emission of fluorescence light. Further to these embodiments, the fluorescence light is passed through dichroic mirror 112 and filter 114, and is further recorded employing CCD camera 106. In an example, laser light from laser source 104 is implemented as a 532 nm diode-pumped solid-state laser light at about 1000 mW (e.g., Shanghai Dream Lasers Co., Ltd., Nan Yao Road, Shanghai, China). In this example, diffuser 110 is implemented as a 5-degree conical diffuser. Further to this example, dichroic mirror 112 is implemented as $\lambda_{crit}$=690 nm. Still further to this example, filter 114 is implemented as a 715 nm long pass filter. In this example, images are recorded at 1000 frames per second employing CCD camera model Little Joe available from SciMeasure Analytical Systems, Inc., Decatur, Ga. 30030, USA.

Figure 2:
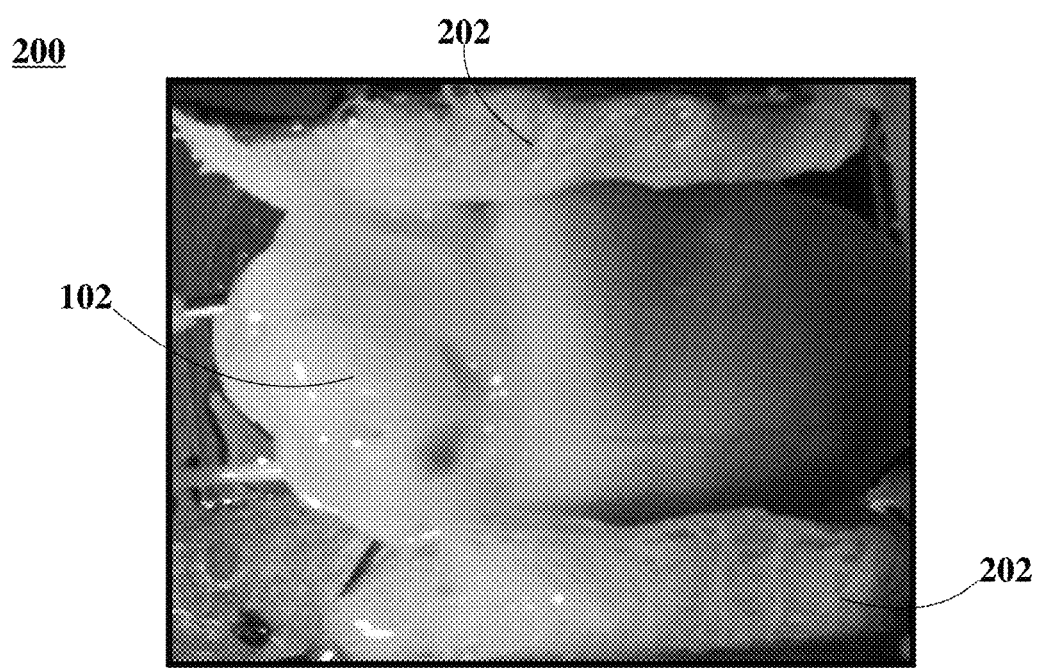
FIG. 2 is a photographic representation depicting the positioning of stimulating electrodes on a Langendorff-perfused rabbit heart, according to an embodiment.

FIG. 2 is a photographic representation depicting the positioning of stimulating electrodes on a Langendorff-perfused rabbit heart, according to an embodiment. In FIG. 2, rabbit heart image 200 includes Langendorff-perfused heart 102 and electrodes 202. In FIG. 2, elements having substantially similar element numbers from previous figures function in a substantially similar manner.

In some embodiments, electrodes 202 are implemented as 2×2 cm aluminum plate electrodes (covered with gauze), which are placed in the epicardium, one touching the right ventricle, and another touching the left ventricle.

In some embodiments, ventricular fibrillation was induced in the Langendorff-perfused heart 102 by placing both terminals of a 9V battery on the right ventricle for about 1 s. In these embodiments, electrodes 202 were then placed on each side of Langendorff-perfused heart 102 to deliver pulses of nanosecond duration to terminate ventricular fibrillation. Further to these embodiments, approximately 5-10 seconds after inducing fibrillation, a 300 ns shock with an amplitude of 2.3 kV (over 3 cm) was delivered to the electrodes to terminate ventricular fibrillation.

Figure 3:
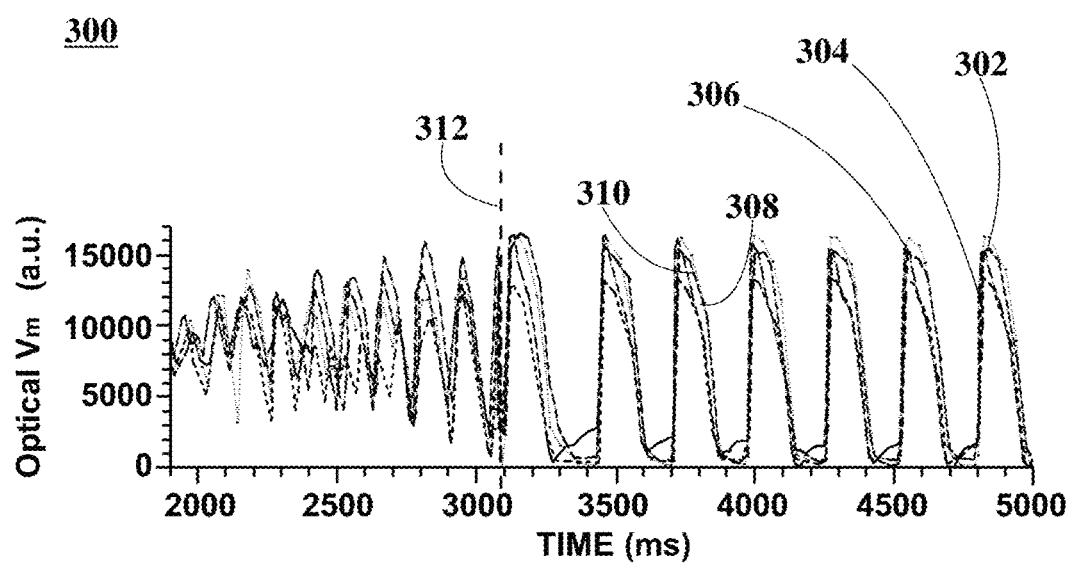
FIG. 3 is an example of successful nsPEF defibrillation captured with optical mapping, and depicted is the optical transmembrane potential measurement (TPM) at a representative surface point of a Langendorff-perfused rabbit heart, according to an embodiment.

FIG. 3 is an example of successful nsPEF defibrillation captured with optical mapping, and depicted is the optical transmembrane potential measurement (TPM) at a representative surface point of a Langendorff-perfused rabbit heart, according to an embodiment. In FIG. 3, optical signal graph 300 includes TPM traces 302, 304, 306, 308, and 310. In FIG. 3, optical signal graph 300 further includes defibrillation shock application point 312.

In some embodiments, TPM traces 302, 304, 306, 308, and 310 illustrate the electrical activity associated with five representative points of the cardiac surface before and after defibrillation shock application point 312. In these embodiments, approximately 5-10 seconds after inducing fibrillation, a 300 ns shock with an amplitude of 2.3 kV (over 3 cm) was delivered to the cardiac surface at application point 312. Further to these embodiments and before the shock (from 0 to approximately 3100 ms), the aforementioned traces are weakly correlated and exhibit frequencies of about 10 Hz, which are typical for fibrillation. Further to these embodiments and after the shock application (at about 3150 ms), all cardiac surface points immediately exhibit synchronized, normal action potentials (APs).

Figure 4:
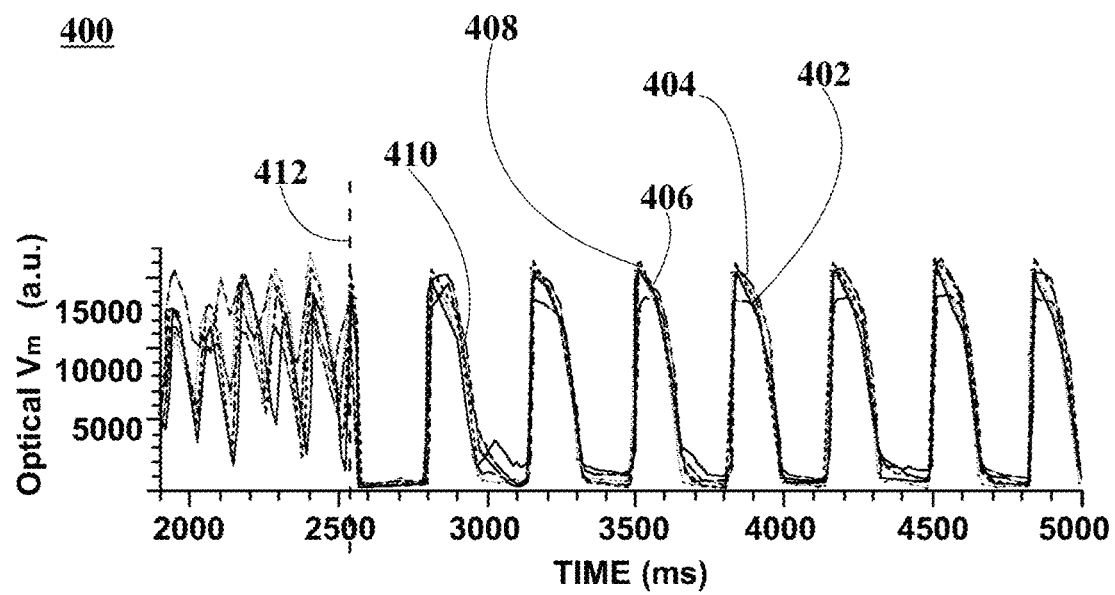
FIG. 4 is a second example of successful nsPEF defibrillation captured with optical mapping, and depicted is the TPM at a representative surface point of a Langendorff-perfused rabbit heart, according to an embodiment.

FIG. 4 is a second example of successful nsPEF defibrillation captured with optical mapping, and depicted is the TPM at a representative surface point of a Langendorff-perfused rabbit heart, according to an embodiment. In FIG. 4, optical signal graph 400 includes TPM traces 402, 404, 406, 408, and 410. In FIG. 4, optical recording 400 further includes defibrillation shock application point 412.

In some embodiments, TPM traces 402, 404, 406, 408, and 410 illustrate the electrical activity associated with five representative points of the cardiac surface before and after defibrillation shock application point 412. In these embodiments, approximately 5-10 seconds after inducing fibrillation, a 300 ns shock with an amplitude of 2.3 kV (over 3 cm) was delivered to the cardiac surface at application point 412. Further to these embodiments and before the shock (from 0 to approximately 2580 ms), the aforementioned traces are weakly correlated and exhibit frequencies of about 10 Hz, which are typical for fibrillation. Further to these embodiments and after the shock application (at about 2800 ms), all cardiac surface points immediately exhibit synchronized, normal APs.

In summary and referring to FIGS. 3 and 4, six (6) successful defibrillation episodes were recorded in three (3) New Zealand rabbit hearts (one not shown) and the defibrillation thresholds were consistently below 2.3 kV (over 3 cm). Further, nanosecond-defibrillation is a promising technology that allows clinical defibrillation employing significantly reduced energy.

Example 2

Twelve (12) New Zealand white rabbits of either sex (3-4 kg) were handled and euthanized according to the approved animal protocol. The twelve rabbits were heparinized (500 IU/kg) and brought to a surgical plane of anesthesia with 2.5-4% isoflurane. The hearts were rapidly removed, the aorta cannulated and flushed with ice cold Tyrode solution (in mM: NaCl: 128.2, $NaCO_3$: 20, $NaH_2PO_4$: 1.2, $MgCl_2$: 1.1, KCl: 4.7, $CaCl_2$: 1.3, glucose: 11.1). The hearts were placed within optical mapping system 100, where they were perfused and superfused with warm oxygenated Tyrode solution (37±0.5° C.) at a constant pressure of 60-80 mmHg. After 30 min equilibration, 10-15 mM of 2, 3-butanedione monoxime was added to eliminate contractions.

Figure 5:
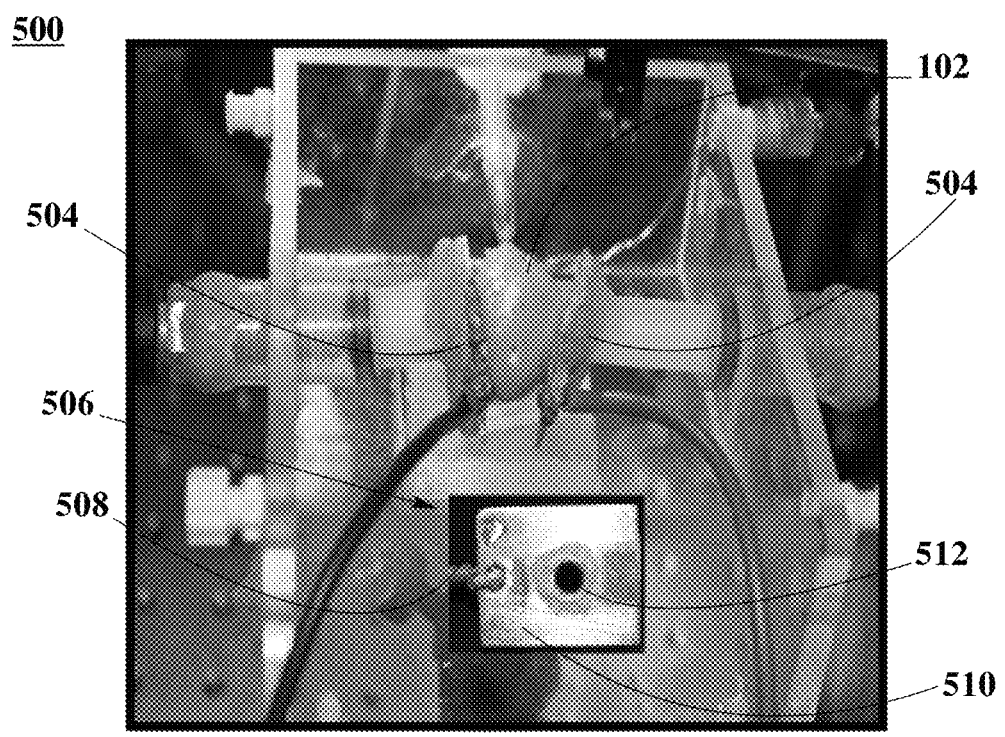
FIG. 5 is a photographic representation depicting a Langendorff-perfused rabbit heart in an optical mapping system, according to an embodiment.

FIG. 5 is a photographic representation depicting a Langendorff-perfused rabbit heart in an optical mapping system, according to an embodiment. In FIG. 5, optical mapping system 500 includes Langendorff-perfused heart 102, electrodes 504, and inset image 506. In an example and referring to FIG. 1B, optical mapping system 500 is implemented as optical mapping system 100. In FIG. 5, inset image 506 is a graphical representation illustrating a special window electrode 508. In FIG. 5, special window electrode 508 includes aluminum plate 510 and hole 512.

In FIG. 5, electrodes 504 are positioned to the left and to the right of Langendorff-perfused heart 102, and the illumination is provided from above Langendorff-perfused heart 102. The fluorescent light is recorded from the top. In some embodiments, electrodes 504 contact Langendorff-perfused heart 102 at the right and left ventricular free wall. In these embodiments, electrodes 504 include special window electrode 508 made for optical mapping of the area directly under the electrodes, as illustrated by inset image 506. Window electrode 508 is implemented as a plate 510 having a hole 512 in the center. In an example, electrodes 504 are implemented as two aluminum plate electrodes including plate 510 and hole 512. In this example, hole 512 is implemented as a 5 mm hole covered with a glass plate that is coated with indium tin oxide (ITO), thereby rendering the glass plate both transparent and electrically conductive. Further to this example, by recording voltage-sensitive fluorescence through special window electrode 508 illustrated in inset image 506, observation of shock-induced electric activity right under the shock electrodes 504 is possible.

In some embodiments, Langendorff-perfused heart 102 is illuminated with a laser light from laser source 104 directed to mirror 108 and then through diffuser 110 and then through dichroic mirror 112 onto Langendorff-perfused heart 102 to achieve uniform illumination. In these embodiments, upon reaching Langendorff-perfused heart 102 and illuminating it, a portion of the laser light is reflected as fluorescence light. Further to these embodiments, the fluorescence light is passed through dichroic mirror 112 and filter 114, and is further recorded employing CCD camera 106. In an example, laser light from laser source 104 is implemented as a 671 nm diode-pumped solid-state laser light at about 1000 mW (e.g., Shanghai Dream Lasers Co., Ltd., Nan Yao Road, Shanghai, China). In this example, diffuser 110 is implemented as a 5-degree conical diffuser. Further to this example, dichroic mirror 112 is implemented as $\lambda_{crit}$=690 nm. Still further to this example, filter 114 is implemented as a 715 nm long pass filter. In this example, images are recorded at 1000 frames per second employing CCD camera model Little Joe available from SciMeasure Analytical Systems, Inc., Decatur, Ga. 30030, USA.

In some embodiments, ventricular fibrillation was induced to the hearts by contacting the ventricular surfaces with two electrodes connected to the poles of a 9V battery. In these embodiments, the two electrodes are gently rubbed on the cardiac surface. Further to these embodiments, fibrillation was considered sustained when it lasted at least 30 seconds after the battery had been removed. In some embodiments, defibrillation shocks of 300 ns with an amplitude of 3 kV (over 3 cm) were applied to all hearts exhibiting sustained ventricular fibrillation. In these embodiments, successful defibrillation of rabbit hearts was accomplished employing single nanosecond pulses of 3 kV (over 3 cm).

Figure 6:
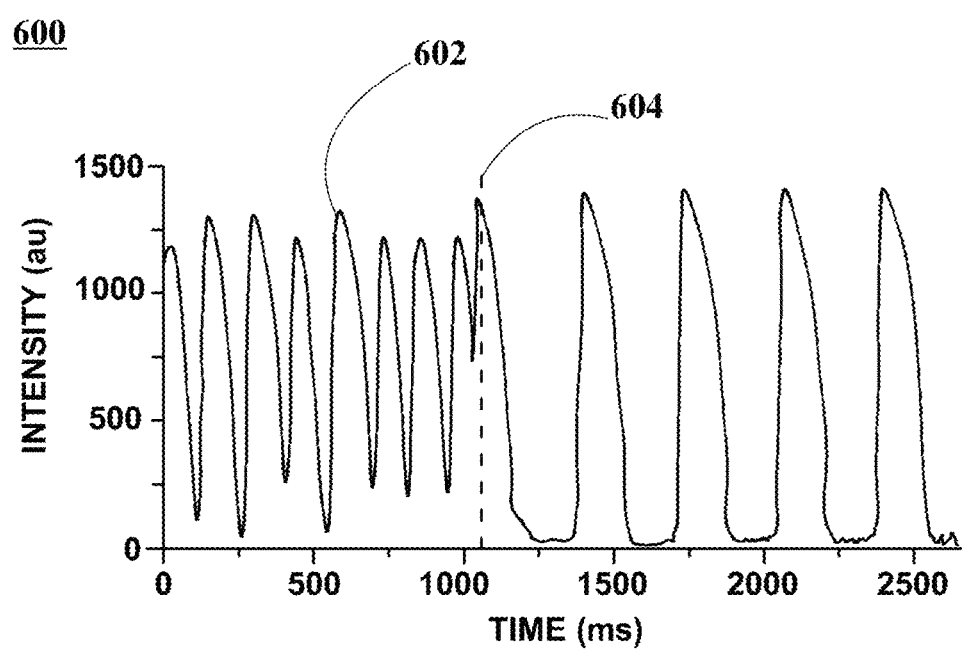
FIG. 6 is a third example of successful nsPEF defibrillation captured with optical mapping, and depicted is the TPM at a representative surface point of a Langendorff-perfused rabbit heart, according to an embodiment.

FIG. 6 is a third example of successful nsPEF defibrillation captured with optical mapping, and depicted is the TPM at a representative surface point of a Langendorff-perfused rabbit heart, according to an embodiment. In FIG. 6, optical signal graph 600 includes TPM trace 602 and defibrillation shock application point 604.

In some embodiments, TPM trace 602 illustrates the electrical activity associated with a representative point of the cardiac surface before and after defibrillation shock application point 604. In these embodiments, a 300 ns shock was delivered to the cardiac surface at application point 604. In these embodiments and before the shock (from 0 to approximately 1000 ms), the aforementioned trace exhibits fast irregular activity, which is distinctive for fibrillation. Further to these embodiments and after the shock application (at about 1050 ms), fibrillation is immediately terminated and the heart is restored to sinus rhythm.

Figure 7:
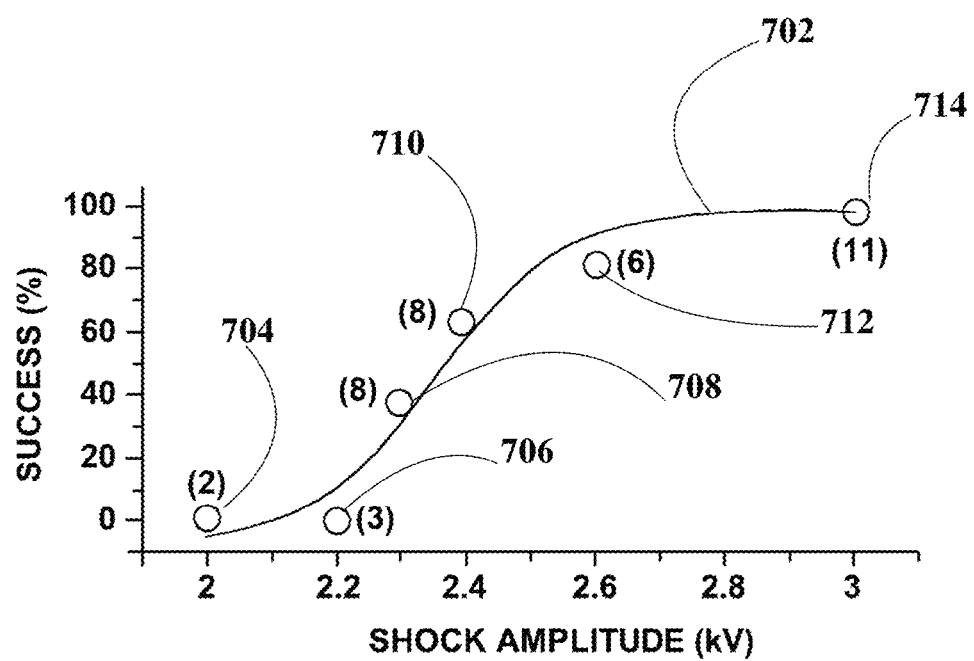
FIG. 7 is a graphical representation illustrating a defibrillation success rate as a function of shock amplitude, according to an embodiment.

FIG. 7 is a graphical representation illustrating defibrillation success rates as a function of shock amplitude, according to an embodiment. In FIG. 7, defibrillation success rate graph 700 includes sigmoidal curve 702 and data points 704, 706, 708, 710, 712, and 714. In FIG. 7, the numbers in parentheses indicate how many observations contributed to each associated data point.

In some embodiments, the defibrillation success rate depends on the amplitude of the shock applied. In these embodiments, successful defibrillation is obtained when applying shocks with amplitudes greater than 2.2 kV (over 3 cm, data points 708, 710, 712, and 714). Further to these embodiments, as illustrated in FIG. 7, the probability of success increases when applying shocks having an amplitude within a range from about 2.3 kV to about 2.6 kV (over 3 cm, data points 708, 710, and 712). Still further to these embodiments, consistent success is obtained when applying shocks having an amplitude of about 3 kV (over 3 cm, data point 714). In an example, the fitted sigmoid curve 702 corresponds to a defibrillation threshold (e.g., 50% defibrillation success) of about 2.3 kV shock amplitude (over 3 cm).

Comparison of nsPEF to Mono- and Biphasic Waveform Defibrillation

In some embodiments, successful defibrillation is achieved when applying nsPEF shocks in which the energy dissipated into the tissue is approximately 56 mJ. In an example, the energy dissipated into the tissue (56 mJ±4 mJ) is calculated based on the formula ($½CU^2$), wherein U is the amplitude of a nsPEF shock (e.g., U=2.3 kV±0.2 kV) and C is the capacitance of the capacitor energy source (e.g., C=21.2 nF). In these embodiments, this defibrillation energy can be directly compared with that of a defibrillation study with biphasic and monophasic millisecond waveforms, which was likewise performed in rabbits and used the same electrode configuration (e.g., one electrode touching the epicardium of the right free ventricular wall, the other electrode touching the epicardium of the left free ventricular wall). Further to these embodiments, the defibrillation thresholds were 530 mJ for monophasic shocks (e.g., 9 times nsPEF threshold). In summary, the energy deposited at the defibrillation threshold was 56 mJ, or approximately 11% of the energy needed for defibrillation with a biphasic ms pulse, and nsPEF shocks reliably terminated fibrillation as illustrated in FIGS. 3 and 4, above. In other embodiments, a research study of rabbit hearts that employed a substantially similar electrode configuration, obtained a similar monophasic threshold of 320 mJ.

Figure 8:
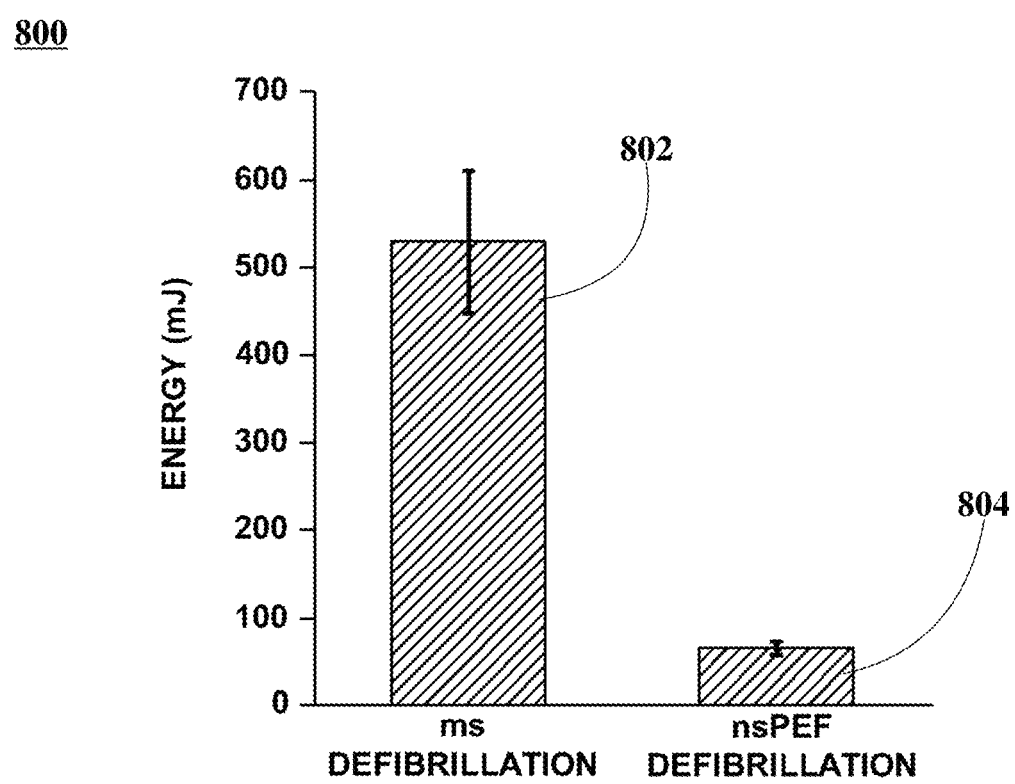
FIG. 8 is a graphical representation illustrating a comparison of defibrillation energy (at threshold) for millisecond defibrillation (monophasic) and nanosecond pulsed electric field (nsPEF) defibrillation, according to an embodiment.

FIG. 8 is a graphical representation illustrating a comparison of defibrillation energy (at threshold) for millisecond defibrillation (monophasic) and nanosecond pulsed electric field (nsPEF) defibrillation, according to an embodiment. In FIG. 8, energy comparison graph 800 includes defibrillation energy bar 802 and defibrillation energy bar 804.

In some embodiments, defibrillation energy bar 802 illustrates the energy required for defibrillation employing a conventional method (e.g., monophasic). In these embodiments, defibrillation energy bar 804 illustrates the energy required for defibrillation employing nsPEF. Further to these embodiments, in order to compare nsPEF defibrillation with conventional defibrillation, the defibrillation threshold for both methods was determined employing a substantially similar electrode configuration and two (2) Langendorff-perfused rabbit hearts. Still further to these embodiments, defibrillation thresholds were 2.3 kV±0.2 kV for nsPEF defibrillation, and 37±2 V for conventional defibrillation. In these embodiments, as illustrated in FIG. 8, the energy required for nsPEF defibrillation (defibrillation energy bar

804) is 56 mJ±4 mJ whereas the energy required for conventional defibrillation (defibrillation energy bar 802) is 530 mJ±35 mJ. Further to these embodiments and referring to FIG. 8, nsPEF defibrillation only requires 11% of the energy required for conventional defibrillation. In these embodiments, this reduction of required energy is particularly impressive when compared to the modest improvements that occurred during the long transition from mono- to biphasic shocks yielded (e.g., 30-50% reduction).

In summary, these results indicate that nsPEFs can indeed defibrillate a fibrillating heart.

Safety of nsPEF

In some embodiments, a variety of markers and/or measurements are used for evaluating tissue, before and after the shock, to determine heart functionality and/or tissue damage from nsPEF treatment. In these embodiments, the markers and/or measurements include: tetrazolium chloride (TTC) staining for dead tissue, shock-induced baseline shift, and spatially resolved parameters of cardiac electrical activity (APD and DI) before and after the shock.

TTC Staining and Sectioning

In some embodiments and for further study of the geometry of the ablated volume, after the creation and electrophysiological evaluation some preparations were lightly frozen (30 minutes at about −30° C.), sectioned into about 2 mm thick slices and immersed in TTC (30 mM) for about 20 minutes. In use, TTC stains live tissue deeply red, while dead cells appear white. In these embodiments, for control experiments 50 µL Titon (5%) was injected into the ventricular walls of two hearts that did not receive electric shocks. Titon is a surfactant that effectively kills cells, and TTC staining of these two hearts exhibited white regions of appropriate size (a few mm in diameter) around the Titon injection site, with all other tissue stained uniformly red. Further to these embodiments, white regions that could indicate shock-induced damage were looked for during the evaluation of hearts that received electric shocks. In these embodiments, the two hearts were sectioned and analyzed for tissue death using the TTC stain. Further to these embodiments, no areas of shock-induced dead tissue were identified in either heart, thereby all the results are consistent with the absence of any tissue damage.

Absence of Baseline Shift

In some embodiments, even though histology studies indicate that all tissue remains viable after nsPEF application, there is still a concern that the electrophysiology of the exposed tissue might be altered due to the nsPEF application. In these embodiments, the major concern is the occurrence of significant electroporation. This condition can be detected using optical mapping as a baseline shift of the signal for affected pixels. Further to these embodiments, if significant electroporation occurs, the affected parts of the tissue are not able to repolarize to their normal resting potential (because leakage currents drive it back a depolarized state). Still further to these embodiments, the optical mapping monitors the transmembrane potential and indicates that the affected parts of the heart will not go back to baseline for the duration of electroporation. In these embodiments, all successful defibrillation recordings were checked for baseline shift. Further to these embodiments, no indication of baseline shift was found in these recordings.

In some embodiments, when looking for electroporation-induced baseline shifts, the most likely location for electroporation is under the electrodes, however, since the imaging of the heart is performed from above, the area under the electrodes was not visible, and the tissue imaged was exposed to a lower electric field. In these embodiments, to address this problem, special electrodes were developed (e.g., electrodes 504) that allow recording of the shock response beneath the shock electrodes. Further to these embodiments, while employing special electrodes 504 35 shock responses (between 1 and 1.5 kV over 3 cm) were recorded from one heart. Still further to these embodiments, the analysis of the responses did not exhibit any sign of baseline shift even at this specific location.

Effects of nsPEF on Normal Physiological Electrical Activity of the Heart

In some embodiments, action potential duration (APD) and diastolic interval (DI) are measured before and after a nsPEF shock application to determine if any changes occurred in the electrical activity of the heart. In these embodiments, the absence of significant permanent changes in APD and DI indicate that the normal physiological electrical activity of the heart is not affected by nsPEF shocks. Further to these embodiments, measurements are taken in locations near the electrodes because tissue in the vicinity of the electrodes is more affected by applied shocks than tissue located further away.

Figure 9:
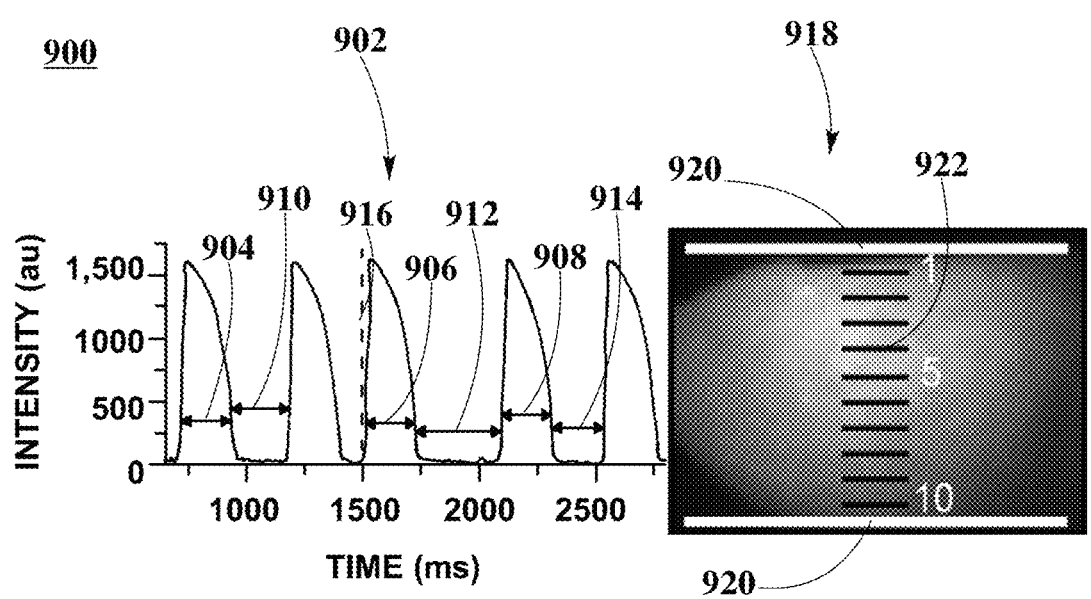
FIG. 9 is a graphical representation illustrating effects of nsPEF stimulation on action potential duration (APD) and diastolic interval (DI) in hearts that exhibit a sinus rhythm, according to an embodiment.

FIG. 9 is a graphical representation illustrating effects of nsPEF stimulation on action potential duration (APD) and diastolic interval (DI) within hearts that exhibit a sinus rhythm, according to an embodiment. In FIG. 9, nsPEF stimulation graphs 900 includes cardiac surface optical signal graph 902 and heart in system 918. In FIG. 9, cardiac surface optical signal graph 902 includes APD 904, APD 906, APD 908, DI 910, DI 912, DI 914, and shock application point 916. In FIG. 9, heart in system 918 includes electrodes position 920 and sample locations 922.

In some embodiments, APD 904 represents an APD of a heart prior to the application of a nsPEF shock. In these embodiments, APD 906 represents a first APD of a heart after the application of a nsPEF shock. Further to these embodiments, APD 908 represents a second APD of a heart after the application of a nsPEF shock. Still further to these embodiments, DI 910 represents a DI of a heart prior to the application of a nsPEF shock. In these embodiments, DI 912 represents a first DI after the application of a nsPEF shock. Further to these embodiments, DI 914 represents a second DI after the application of the nsPEF shock. Still further to these embodiments, shock application point 916 illustrates the moment when the nsPEF shock is applied to the heart.

In some embodiments, electrodes position 920 illustrates the part of the heart where the shock electrodes are located. In these embodiments, sample locations 922 illustrate the locations of the heart where the APD and DI are measured for evaluation. Further to these embodiments, sample locations 922 include ten different locations in the cardiac tissue (marked in black).

Figure 10:
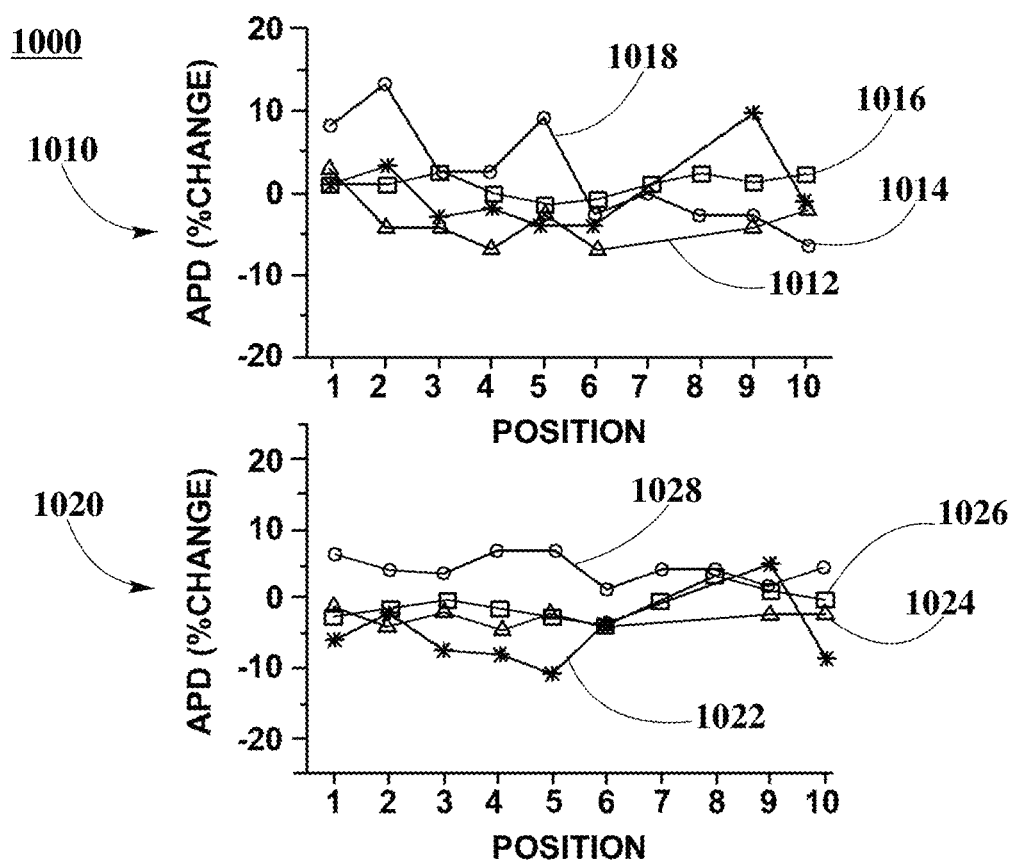
FIG. 10 is a graphical representation illustrating percentage changes of APD in four hearts before and after the application of a nsPEF shock with APD measurements taken at ten different locations as illustrated in FIG. 9, according to an embodiment.

FIG. 10 is a graphical representation illustrating percentage changes of APD in four hearts before and after the application of a nsPEF shock with APD measurements taken at ten different locations as illustrated in FIG. 9, according to an embodiment. In FIG. 10, APD comparison graph 1000 includes first APD comparison graph 1010 and second APD comparison graph 1020. In FIG. 10, first APD comparison graph 1010 includes APD comparison lines 1012, 1014, 1016, and 1018. In FIG. 10, second APD comparison graph 1020 includes APD comparison lines 1022, 1024, 1026, and 1028.

In some embodiments, APD comparison lines 1012, 1014, 1016, and 1018 illustrate the percentage changes of APD within four (4) hearts as a comparison of the first APD after the application of a nsPEF shock (APD 906) to the APD prior to the application of the shock (APD 904). In these embodiments, each APD comparison line represents the APD percentage changes in a single heart with the measurements taken at the ten different locations illustrated in FIG. 9, above.

In some embodiments and referring to first APD comparison graph 1010, 3 hearts exhibit changes of APD below 5% in all observation points (APD comparison lines 1012, 1014, and 1016), while 1 heart exhibits changes of APD in the range of 5-10% in 9 observation points and a single observation point above 10% (APD comparison line 1018). In these embodiments, the average change of APD for all hearts was 3.5%. Further to these embodiments, APD percentage change differences are substantially similar to differences in hearts that have not been exposed to electric shocks. Still further to these embodiments, there is no systematic bias of the changes towards certain electrode positions. In these embodiments, there is no evidence for stronger effects in the vicinity of the electrodes (samples location 922), which would be the most likely location for damage due to applied fields.

In some embodiments, APD comparison lines 1022, 1024, 1026, and 1028 illustrate the percentage changes of APD within four (4) hearts as a comparison of the second APD after the application of the nsPEF shock (APD 908) to the APD prior to the application of the shock (APD 904). In these embodiments, each APD comparison line represents the APD percentage changes in a single heart with the measurements taken at the ten different locations as illustrated in FIG. 9, above.

In some embodiments and referring to second APD comparison graph 1020, all hearts exhibit changes of APD in the range of 1-8% in all observation points (APD comparison lines 1022, 1024, 1026, and 1028). In these embodiments, all hearts exhibit changes of APD with an overall average of 3.65%. Further to these embodiments, APD percentage change differences are substantially similar to differences in hearts that have not been exposed to electric shocks. Still further to these embodiments, there is no systematic bias of the changes towards certain electrode positions. In these embodiments, there is no evidence for stronger effects close to the electrodes (samples location 922), which is a major concern.

Figure 11:
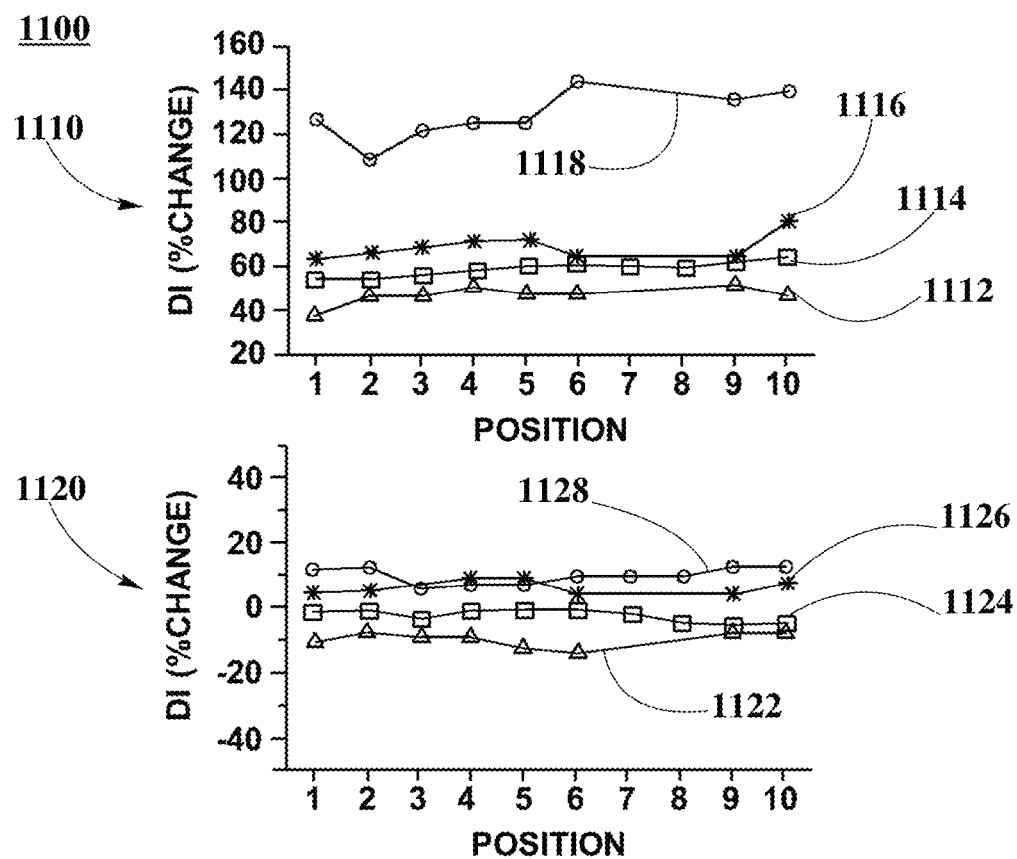
FIG. 11 is a graphical representation illustrating percentage changes of DI in four hearts before and after the application of a nsPEF shock with DI measurements taken at ten different locations, according to an embodiment.

FIG. 11 is a graphical representation illustrating percentage changes of DI in four hearts before and after the application of a nsPEF shock with DI measurements taken at ten different locations as illustrated in FIG. 9, according to an embodiment. In FIG. 11, DI comparison graph 1100 includes first DI comparison graph 1110 and second DI comparison graph 1120. In FIG. 11, first DI comparison graph 1110 includes DI comparison lines 1112, 1114, 1116, and 1118. In FIG. 11, second DI comparison graph 1120 includes DI comparison lines 1122, 1124, 1126, and 1128.

In some embodiments, DI comparison lines 1112, 1114, 1116, and 1118 illustrate the percentage changes of DI within four (4) hearts as a comparison of the first DI after the application of a nsPEF shock (DI 912) to the DI prior to the application of the shock (DI 910). In these embodiments, each DI comparison line represents the DI percentage changes in a single heart with the measurements taken at the ten different locations as illustrated in FIG. 9, above.

In some embodiments and referring to first DI comparison graph 1110, all hearts exhibit changes of DI between 40% and 140% (DI comparison lines 1112, 1114, 1116, and 1118) with an overall average of 70.6%. In these embodiments, DI percentage change differences are significantly above typical variations for hearts that have not been exposed to electric shocks. Further to these embodiments, there is no systematic bias of the changes towards certain electrode positions.

In some embodiments, DI comparison lines 1122, 1124, 1126, and 1128 illustrate the percentage changes of DI within four (4) hearts as a comparison of the second DI after the application of the nsPEF shock (DI 914) to the DI prior to the application of the shock (DI 910). In these embodiments, each DI comparison line represents the DI percentage changes in a single heart with the measurements taken at the ten different locations as illustrated in FIG. 9, above.

In some embodiments and referring to second DI comparison graph 1120, all hearts exhibit changes of DI below 10% (DI comparison lines 1122, 1124, 1126, and 1128) with an overall average of 6.98%. In these embodiments, DI percentage change differences are substantially similar to differences in hearts that have not been exposed to electric shocks. Further to these embodiments, there is no systematic bias of the changes towards certain electrode positions. Still further to these embodiments, there are no permanent changes in DI after the application of nsPEF shock since the DI increase observed within first DI comparison graph 1110 was transient.

Figure 12:
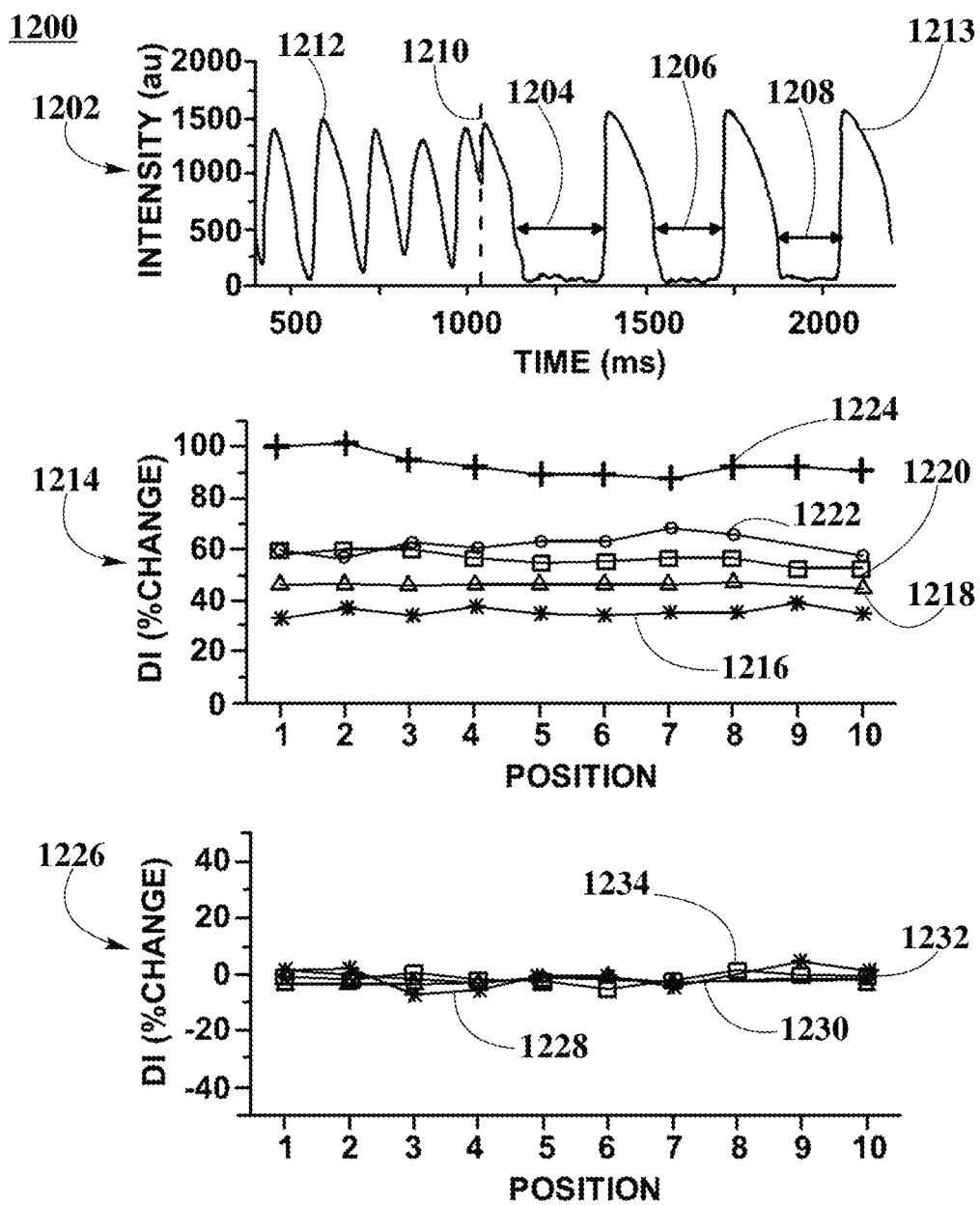
FIG. 12 is a graphical representation illustrating effects of a nsPEF defibrillation on DI, according to an embodiment.

FIG. 12 is a graphical representation illustrating effects of a nsPEF defibrillation on DI, according to an embodiment. In FIG. 12, nsPEF defibrillation effect 1200 includes cardiac surface optical signal graph 1202, first DI comparison graph 1214, and second DI comparison graph 1226. In FIG. 12, cardiac surface optical signal graph 1202 includes DI 1204, DI 1206, DI 1208, shock application point 1210, fibrillation pattern 1212, and sinus pattern 1213. In FIG. 12, first DI comparison graph 1214 includes DI comparison lines 1216, 1218, 1220, 1222, and 1224 associated with five (5) hearts. In FIG. 12, second DI comparison graph 1226 includes DI comparison line 1228, 1230, 1232, and 1234 associated with four (4) hearts.

In some embodiments, DI 1204 represents a first DI of a heart after the application of a nsPEF shock (shock application point 1210). In these embodiments, DI 1206 represents a second DI after the application of the nsPEF shock. Further to these embodiments, DI 1208 represents a third DI after the application of the nsPEF shock. Still further to these embodiments, shock application point 1210 illustrates a moment when the nsPEF shock is applied to the heart. In these embodiments, fibrillation pattern 1212 illustrates an electrical signal of a fibrillating heart before nsPEF defibrillation, and sinus pattern 1213 illustrates an electrical signal of a heart in sinus rhythm after application of nsPEF treatment.

In some embodiments, DI comparison lines 1216, 1218, 1220, 1222, and 1224 illustrate the percentage changes of DI associated with DI 1206 with respect to DI 1204. In these embodiments, each DI comparison line represents the DI percentage changes in one heart with the measurements taken at ten different locations as illustrated in FIG. 9, above.

In some embodiments and referring to first DI comparison graph 1214, all hearts exhibit changes of DI between 30% and 100% with an overall average of 58.9%. In these embodiments, DI percentage change differences are significantly above typical variations for hearts that have not been exposed to electric shocks. Further to these embodiments, there is no systematic bias of the changes towards certain electrode positions.

In some embodiments, DI comparison lines 1228, 1230, 1232, and 1234 illustrate the percentage changes of DI associated with DI 1208 with respect to DI 1206. In these embodiments, each DI comparison line represents the DI percentage changes in one heart with the measurements taken at ten different locations as illustrated in FIG. 9, above.

In some embodiments and referring to second DI comparison graph 1226, all hearts exhibit changes of DI below 10% with an overall average of 2.26%. In these embodiments, DI percentage change differences are substantially similar to differences in hearts that have not been exposed to electric shocks. Further to these embodiments, there is no systematic bias of the changes towards certain electrode positions. Still further to these embodiments, there are no permanent changes in DI after the application of nsPEF shock since the DI increase observed within first DI comparison graph 1214 was transient.

In summary, nsPEF defibrillation demonstrates its effectiveness as a new defibrillation modality, thereby achieving reliable defibrillation with energies that are an order of magnitude smaller than those needed for conventional defibrillation (e.g., mono and bi-phasic waveforms). Further, nsPEF defibrillation did not negatively affect tissue, did not exhibit a baseline shift within the optical transmembrane potential signal (a distinctive feature which indicates electroporation), or affect the (APD) or shape. Additionally, the DI following a shock-induced activation was notably prolonged, but only for a single beat. Finally, the mechanism for nsPEF defibrillation is different from conventional defibrillation since it does not rely on membrane charging, but on the basis of displacement currents that flow within nanoseconds after the shock is applied.

Like biphasic shocks two decades ago, nsPEF may ultimately provide the technology for the next generation of defibrillators that help EMS to treat patients more effectively and ultimately save more patients who experience out-of-hospital cardiac arrests.

While various embodiments of the present disclosure have been described above, it should be understood that they have been presented by way of example only, and not limitation. Numerous changes to the disclosed embodiments can be made in accordance with the disclosure herein without departing from the spirit or scope of the disclosure. Thus, the breadth and scope of the present disclosure should not be limited by any of the above described embodiments.

Rather, the scope of the disclosure should be defined in accordance with the following claims and their equivalents.

Although the present disclosure has been illustrated and described with respect to one or more implementations, equivalent alterations and modifications can occur to others skilled in the art upon the reading and understanding of this specification and the drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

REFERENCES

The following references describe certain aspects of the various embodiments and are all herein incorporated by reference in their entirety:

[1] Go A S, Mozaffarian D, Roger V L, Benjamin E J, Berry J D, Blaha M J, Dai S, Ford E S, Fox C S, Franco S, Fullerton H J, Gillespie C, Hailpern S M, Heit J A, Howard V J, Huffman M D, Judd S E, Kissela B M, Kittner S J, Lackland D T, Lichtman J H, Lisabeth L D, Mackey R H, Magid D J, Marcus G M, Marelli A, Matchar D B, McGuire D K, Mohler E R, 3rd, Moy C S, Mussolino M E, Neumar R W, Nichol G, Pandey D K, Paynter N P, Reeves M J, Sorlie P D, Stein J, Towfighi A, Turan T N, Virani S S, Wong N D, Woo D, Turner M B. Heart disease and stroke statistics—2014 update: a report from the American Heart Association. Circulation 2014; 129(3):e28-e292.

[2] Nichol G, Thomas E, Callaway C W, Hedges J, Powell J L, Aufderheide T P, Rea T, Lowe R, Brown T, Dreyer J, Davis D, Idris A, Stiell I. Regional variation in out-of-hospital cardiac arrest incidence and outcome. JAMA: the journal of the American Medical Association 2008; 300 (12):1423-1431.

[3] Rantner L J, Tice B M, Trayanova N A. Terminating ventricular tachyarrhythmias using far-field low-voltage stimuli: Mechanisms and delivery protocols. Heart Rhythm 2013; 10(8):1209-1217.

[4] Sowell B, Fast V G. Ionic mechanism of shock-induced arrhythmias: Role of intracellular calcium. Heart Rhythm 2012; 9(1):96-104.

[5] Kodama I, Sakuma I, Shibata N, Honjo H, Toyama J. Arrhythmogenic changes in action potential configuration in the ventricle induced by DC shocks. J Electrocardiol 1999; 32:92-99.

[6] Kodama I, Sakuma I, Shibata N, Knisley S B, Niwa R, Honjo H. Regional differences in arrhythmogenic aftereffects of high intensity DC stimulation in the ventricles. Pace 2000; 23(5):807-817.

[7] Goncalves J, Pereira T. Inappropriate Shocks in Patients with ICDs: Single Chamber versus Dual Chamber. Arq Bras Cardiol 2013; 101(2):141-148.

[8] Al-Khadra A, Nikolski V, Efimov I R. The role of electroporation in defibrillation. Circ Res 2000; 87(9): 797-804.

[9] Nikolski V P, Efimov I R. Electroporation of the heart. Europace: European pacing, arrhythmias, and cardiac electrophysiology: journal of the working groups on cardiac pacing, arrhythmias, and cardiac cellular electrophysiology of the European Society of Cardiology 2005; 7 Suppl 2:146-154.

[10] Wang Y T, Efimov I R, Cheng Y N. Electroporation induced by internal defibrillation shock with and without recovery in intact rabbit hearts. Am J Physiol-Heart C 2012; 303(4):H439-H449.

[11] Tan V H, Wilton S B, Kuriachan V, Sumner G L, Exner D V. Impact of Programming Strategies Aimed at Reducing Nonessential Implantable Cardioverter Defibrillator Therapies on Mortality A Systematic Review and Meta-Analysis. Circ-Arrhythmia Elec 2014; 7(1):164-170.

[12] Tokano T, Bach D, Chang J, Davis J, Souza J J, Zivin A, Knight B P, Goyal R, Man K C, Morady F, Strickberger S A. Effect of ventricular shock strength on cardiac hemodynamics. J Cardiovasc Electr 1998; 9(8):791-797.

[13] Bradfield J S, Buch E, Shivkumar K. Interventions to decrease the morbidity and mortality associated with implantable cardioverter-defibrillator shocks. Curr Opin Crit Care 2012; 18(5):432-437.

[14] Xie J L, Weil M H, Sun S J, Tang W C, Sato Y J, Jin X H, Bisera J. High-energy defibrillation increases the severity of postresuscitation myocardial dysfunction. Circulation 1997; 96(2):683-688.

[15] Berg M D, Banville I L, Chapman F W, Walker R G, Gaballa M A, Hilwig R W, Samson R A, Kern K B, Berg R A. Attenuating the defibrillation dosage decreases postresuscitation myocardial dysfunction in a swine model of pediatric ventricular fibrillation. Pediatr Crit Care Me 2008; 9(4):429-434.

[16] Kern K B. Postresuscitation myocardial dysfunction. Cardiol Clin 2002; 20(1):89-101.

[17] Tewelde S Z, Winters M E. Cooling the Fire Resuscitated Sudden Death. Cardiol Clin 2012; 30(4):639.

[18] Laurent I, Monchi M, Chiche J D, Joly L M, Spaulding C, Bourgeois N, Cariou A, Rozenberg A, Carli P, Weber S, Dhainaut J F. Reversible myocardial dysfunction in survivors of out-of-hospital cardiac arrest. J Am Coll Cardiol 2002; 40(12):2110-2116.

[19] Neumar R W, Nolan J P, Adrie C, Aibiki M, Berg R A, Bottiger B W, Callaway C, Clark R S B, Geocadin R G, Jauch E C, Kern K B, Laurent I, Longstreth W T, Merchant R M, Morley P, Morrison L J, Nadkarni V, Peberdy M A, Rivers E P, Rodriguez-Nunez A, Sellke F W, Spaulding C, Sunde K, Hoek T V. Post-Cardiac Arrest Syndrome Epidemiology, Pathophysiology, Treatment, and Prognostication A Consensus Statement From the International Liaison Committee on Resuscitation (American Heart Association, Australian and New Zealand Council on Resuscitation, European Resuscitation Council, Heart and Stroke Foundation of Canada, Inter-American Heart Foundation, Resuscitation Council of Asia, and the Resuscitation Council of Southern Africa); the American Heart Association Emergency Cardiovascular Care Committee; the Council on Cardiovascular Surgery and Anesthesia; the Council on Cardiopulmonary, Perioperative, and Critical Care; the Council on Clinical Cardiology; and the Stroke Council. Circulation 2008; 118(23):2452-2483.

[20] Rantner L J, Tice B M, Trayanova N A. Terminating ventricular tachyarrhythmias using far-field low-voltage stimuli: Mechanisms and delivery protocols. Heart Rhythm 2013; 10(8):1209-1217.

[21] Luther S, Fenton F H, Kornreich B G, Squires A., Bittihn P, Hornung D, Zabel M, Flanders J, Gladuli A, Campoy L, Cherry E M, Luther G, Hasenfuss G, Krinsky V I, Pumir A, Gilmour R F, Jr., Bodenschatz E. Low-energy control of electrical turbulence in the heart. Nature 2011; 475(7355):235-239.

[22] Gray R A, Wikswo J P. Cardiovascular diseases. Several small shocks beat one big one. Nature 2011; 475(7355): 181-182.

[23] Tibballs J, Carter B, Kiraly N J, Ragg P, Clifford M. External and internal biphasic direct current shock doses for pediatric ventricular fibrillation and pulseless ventricular tachycardia. Pediatr Crit Care Me 2011; 12(1): 14-20.

[24] Didon J P, Fontaine G, White R D, Jekova I, Schmid J J, Cansell A. Clinical experience with a low-energy pulsed biphasic waveform in out-of-hospital cardiac arrest. Resuscitation 2008; 76(3):350-353.

[25] van Rees J B, Borleffs C J W, de Bie M K, Stijnen T, van Erven L, Bax J J, Schalij M J. Inappropriate Implantable Cardioverter-Defibrillator Shocks Incidence, Predictors, and Impact on Mortality. J Am Coll Cardiol 2011; 57(5):556-562.

[26] Tzeis S, Andrikopoulos G, Kolb C, Vardas P E. Tools and strategies for the reduction of inappropriate implantable cardioverter defibrillator shocks. Europace: European pacing, arrhythmias, and cardiac electrophysiology: journal of the working groups on cardiac pacing, arrhythmias, and cardiac cellular electrophysiology of the European Society of Cardiology 2008; 10(11): 1256-1265.

[27] Tang W, Weil M H, Sun S, Povoas H P, Klouche K, Kamohara T, Bisera J. A comparison of biphasic and monophasic waveform defibrillation after prolonged ventricular fibrillation. Chest 2001; 120(3):948-954.

[28] Clark C B, Zhang Y, Davies L R, Karlsson G, Kerber R E. Transthoracic biphasic waveform defibrillation at very high and very low energies: a comparison with monophasic waveforms in an animal model of ventricular fibrillation. Resuscitation 2002; 54(2):183-186.

[29] Kudenchuk P J, Cobb L A, Copass M K, Olsufka M, Maynard C, Nichol G. Transthoracic incremental monophasic versus biphasic defibrillation by emergency responders (TIMBER): a randomized comparison of monophasic with biphasic waveform ascending energy defibrillation for the resuscitation of out-of-hospital cardiac arrest due to ventricular fibrillation. Circulation 2006; 114(19):2010-2018.

[30] Mittal S, Ayati S, Stein K M, Knight B P, Morady F, Schwartzman D, Cavlovich D, Platia E V, Calkins H, Tchou P J, Miller J M, Wharton J M, Sung R J, Slotwiner D J, Markowitz S M, Lerman B B. Comparison of a novel rectilinear biphasic waveform with a damped sine wave monophasic waveform for transthoracic ventricular defibrillation. ZOLL Investigators. J Am Coll Cardiol 1999; 34(5):1595-1601.

[31] Tanabe S, Yasunaga H, Ogawa T, Koike S, Akahane M, Horiguchi H, Hatanaka T, Yokota H, Imamura T. Comparison of Outcomes After Use of Biphasic or Monophasic Defibrillators Among Out-of-Hospital Cardiac Arrest Patients A Nationwide Population-Based Observational Study. Circ-Cardiovasc Qual 2012; 5(5):689-696.

[32] Luther S, Fenton F H, Kornreich B G, Squires A., Bittihn P, Hornung D, Zabel M, Flanders J, Gladuli A, Campoy L, Cherry E M, Luther G, Hasenfuss G, Krinsky V I, Pumir A, Gilmour R F, Jr., Bodenschatz E. Low-energy control of electrical turbulence in the heart. Nature 2011; 475(7355):235-239.

[33] Gray R A, Wikswo J P. Cardiovascular disease. Several small shocks beat one big one. Nature 2011; 475(7355): 181-182.

[34] Pandit S V. Alternating current for defibrillation therapy: time for reconsideration? Heart Rhythm 2013; 10(5):749-750.

[35] Roberts S J, Guan D, Malkin R. The defibrillation efficacy of high frequency alternating current sinusoidal waveforms in guinea pigs. Pacing and clinical electrophysiology: PACE 2003; 26(2 Pt 1):599-604.

[36] Rosenheck S, Gorni S, Katz I, Rabin A, Shpoliansky U, Mandelbaum M, Weiss A T. Modified alternating current defibrillation: a new defibrillation technique. Europace: European pacing, arrhythmias, and cardiac electrophysiology: journal of the working groups on cardiac pacing, arrhythmias, and cardiac cellular electrophysiology of the European Society of Cardiology 2009; 11(2):239-244.

[37] Weinberg S H, Chang K C, Zhu R, Tandri H, Berger R D, Trayanova N A, Tung L. Defibrillation success with high frequency electric fields is related to degree and location of conduction block. Heart Rhythm 2013; 10(5): 740-748.

What is claimed is:

1. A method of defibrillation of a heart comprising:
   using an external system comprising a nanosecond pulsed electric field (nsPEF) generator and electrodes; and,
   delivering electrical stimulation to terminate fibrillation in the heart experiencing the fibrillation, the electrical stimulation having an electric field sufficient to restore normal electrical activity of the heart but with a reduced defibrillation energy up to 10 times relative to conventional defibrillation, while avoiding ablating heart tissue and without substantial permanent changes in either one or both of action potential duration or diastolic interval,
   wherein the electrical stimulation comprising at least one or more electrical pulses having a pulse duration from about 1 nanosecond to about 1,000 nanoseconds, and further having pulse amplitudes ranging from about 0.01 kV to about 100 kV.

2. The method of claim 1, wherein displacement currents flowing after electrical stimulation results in changes in transmembrane voltage of the heart.

3. The method of claim 1, wherein electrical energy deposited into the heart after electrical stimulation is in the range of about 1 mJ to about 500 J.

4. The method of claim 1, wherein the electrical stimulation reversibly opens pores within cell membranes.

5. The method of claim 4, wherein the pores are cation-selective.

6. The method of claim 4, wherein the pores result in membrane hyperpolarization and reduced excitability.

7. The method of claim 1, the method comprising reducing whole-cell currents through voltage gated Na+ and Ca2+ channels.

8. The method of claim 1, the method comprising using dielectric displacement to achieve uniform activation of tissue of the heart.

9. The method of claim 1, wherein no tissue damage or tissue death occurs after restoring normal electrical activity of the heart by the electrical stimulation.

10. The method of claim 1, wherein the method is used to treat ventricular fibrillation or ventricular tachycardia.

11. A method of defibrillation of a heart, comprising:
    delivering electric stimulation to terminate fibrillation in the heart using an external system comprising a nanosecond pulsed electric field (nsPEF) generator and electrodes,
    the electrical stimulation having an electric field sufficient to restore normal electrical activity of the heart but with a reduced defibrillation energy up to 10 times relative to conventional defibrillation, while avoiding ablating heart tissue and without substantial permanent changes in either one or both of action potential duration or diastolic interval;
    wherein the electric stimulation comprises applying one or more nanosecond pulsed electric fields having a pulse duration from about 1 nanosecond to about 1,000 nanoseconds, and further having pulse amplitudes ranging from about 0.01 kV to about 100 kV.

12. The method of claim 11, wherein displacement currents flowing after delivery of the electric stimulation results in changes in transmembrane voltage of the heart.

13. The method of claim 11, wherein electrical energy deposited into the heart is in the range of about 1 mJ to about 500 J.

14. The method of claim 11, wherein delivery of the electric stimulation reversibly opens pores within cell membranes.

15. The method of claim 14, wherein the pores are cation-selective.

16. The method of claim 14, wherein the pores result in membrane hyperpolarization and reduced excitability.

17. The method of claim 11, the method comprising reducing whole-cell currents through voltage gated Na+ and Ca2+ channels.

18. The method of claim 11, wherein dielectric displacement is used to achieve uniform activation of tissue of the heart.

19. The method of claim 11, wherein no tissue damage or tissue death occurs after restoring normal electrical activity of the heart by the therapeutic dose.

* * * * *